United States Patent [19]

Henniger

[11] 4,010,264
[45] Mar. 1, 1977

[54] 7-[3-SUBSTITUTED ISOXAZOL-5-YL]-ACETAMIDO-CEPHALOSPORANIC ACIDS AND THEIR ANTI-BACTERIAL USE

[75] Inventor: Peter Wolfgang Henniger, Leiden; Peter Max Smid, Delft, both of Netherlands

[73] Assignee: Koninklijke Nederlandsche Gist-en Spiritusfabriek N.V., Delft, Netherlands

[22] Filed: Dec. 17, 1974

[21] Appl. No.: 533,708

Related U.S. Application Data

[63] Continuation-in-part of Ser. No. 195,482, Nov. 3, 1971, Pat. No. 3,891,635.

[30] Foreign Application Priority Data

Nov. 6, 1970 United Kingdom ............ 53040/70

[52] U.S. Cl. .................. 424/246; 260/243 C; 260/239.1; 424/271
[51] Int. Cl.² ............. C07D 501/20; A61K 31/545
[58] Field of Search ................. 424/246; 260/243 C

[56] References Cited

UNITED STATES PATENTS 3,516,997  6/1970  Takano et al. ............... 260/243 C

OTHER PUBLICATIONS

Hackh's Chemical Dictionary (Fourth Ed.), p. 248, (1969).

Primary Examiner—Nicholas S. Rizzo
Attorney, Agent, or Firm—Hammond & Littell

[57] ABSTRACT

Novel heterocyclic amides of the formula

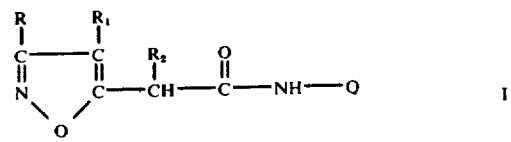

wherein R is selected from the group consisting of lower alkyl and aryl optionally substituted with at least one member of the group consisting of chlorine, fluorine, nitro, amino and lower alkyl and a tertiary alkyl group, $R_1$ is selected from the group consisting of hydrogen, lower alkyl, carboxyl, lower alkoxycarbonyl, an alkali metal, alkaline earth metal or amine salt of carboxyl, a carbamyl, cyano, an amino and chlorine, $R_2$ is selected from the group consisting of hydrogen, halogen, cyano, an amino, lower aralkoxycarbonylamino, lower alkyl, carboxyl esterified with lower alkyl, aryl or aralkyl and carbamoyl optionally substituted on the nitrogen atom with lower alkyl or a phenyl and Q is selected from the group consisting of

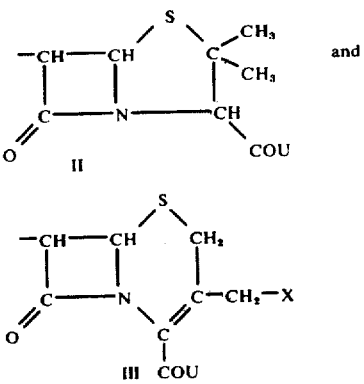

X is selected from the group consisting of hydrogen, hydroxy and lower alkanoyloxy and U is selected from the group consisting of amido forming groups or a group OY, wherein Y is selected from the group consisting of hydrogen, salt forming groups, and ester forming groups, or COOY and $CH_2X$ together form a lactone or lactam, having antibacterial properties, their preparation and novel intermediates thereof.

11 Claims, No Drawings

7-[3-SUBSTITUTED ISOXAZOL-5-YL]-ACETAMIDO-CEPHALOSPORANIC ACIDS AND THEIR ANTI-BACTERIAL USE

PRIOR APPLICATION

The present application is a continuation-in-part of our copending, commonly assigned application Ser. No. 195,482, filed Nov. 3, 1971, now U.S. Pat. No. 3,891,635.

OBJECTS OF THE INVENTION

It is an object of the invention to provide novel heterocyclic compounds of formula I.

It is another object of the invention to provide processes for the preparation of the heterocyclic compounds of formula I and to novel intermediates produced therein.

It is a further object of the invention to provide novel antibacterial compositions and to provide a novel method of combatting bacterial infections in warm-blooded animals.

These and other objects and advantages of the invention will become obvious from the following detailed description.

THE INVENTION

The novel heterocyclic compositions of the invention have the formula

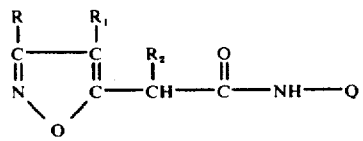

wherein R is selected from the group consisting of lower alkyl and aryl optionally substituted with at least one member of the group consisting of chlorine, fluorine, nitro, amino and lower akyl and a tertiary alkyl group, $R_1$ is selected from the group consisting of hydrogen, lower akyl, carboxyl, lower alkoxycarbonyl, an alkali metal, alkaline earth metal or amine salt of carboxyl, a carbamyl, cyano, an amino and chlorine, $R_2$ is selected from the group consisting of hydrogen, halogen, cyano, an amino, lower aralkoxycarbonylamino, lower alkyl, carboxyl esterified with lower alkyl, aryl or aralkyl and carbamoyl optionally substituted on the nitrogen atom with lower alkyl or a phenyl and Q is selected from the group consisting of

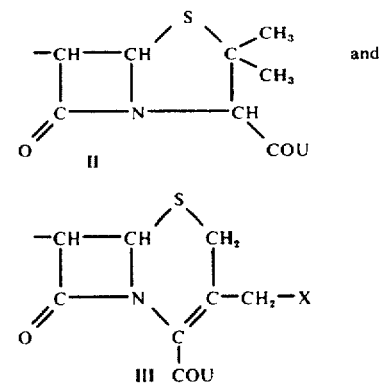

X is selected from the group consisting of hydrogen, hydroxy and lower alkanoyloxy and U is selected from the group consisting of amido forming groups or a group OY wherein Y is selected from the group consisting of hydrogen, salt forming groups, ester forming groups, or COOY and $CH_2X$ together form a lactone or lactam. The term "lower" is intended to mean 1 to 4 carbon atoms.

Among the preferred substituents of formula I, R is lower akyl, phenyl or naphthyl optionally substituted with one or more of chlorine, fluorine, nitro, amino or lower alkyl, preferably 2,6-dichlorophenyl or tertiary alkyl such as adamantyl, $R_1$ is hydrogen, lower alkyl, —COOY' where Y' is hydrogen, lower alkyl, alkali metal, alkaline earth metal or an amino group, carbamoyl, cyano, amino or chlorine and $R_2$ is hydrogen, —CN, amino, lower aralkoxycarbonylamino, lower akyl, lower alkoxycarbonyl, phenyl, lower aralkyl such as benzyl and carbamoyl optionally substituted on the nitrogen atom with lower alkyl or phenyl, X may be hydrogen, —OH or lower alkanoyloxy such as acetoxy, or —$CH_2X$ together with the —COOH group may form

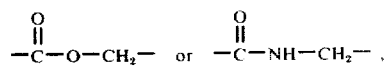

and U is an amide forming group such as —$NH_2$, saccharinyl, succinimido, phtalimido or a group OY, wherein Y is hydrogen, alkali metal, alkaline earth metal or amine salts, an ester group such as tri(lower) alkylsilyl, di(lower)alkylmonohalosilyl, benzyl, phenacyl or lower akyl.

The term "lower" as applied to alkyl or alkanoyl is intended to mean 1 to 4 carbon atoms.

The compounds of formula I may be prepared by several different methods, each of which is an application of a method known in the art for the preparation of penicillins and cephalosporins. According to a feature of the invention, the compounds of formula I are prepared by reacting a salt, ester of a 6-aminopenicillanic or 7-aminocephalosporanic acid compound of the formula:

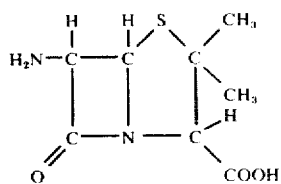

or

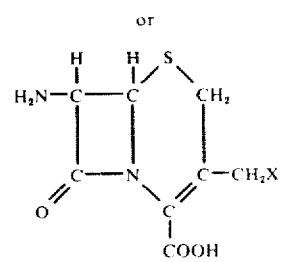

(wherein X is as defined above) with the substituent X when a hydroxy group preferably protected, with an active ester (e.g. 2,4-dinitrophenyl ester, p-nitrophenyl ester of N-hydroxysuccinimide ester) with an acid of the formula:

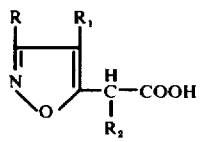

VI wherein R, R$_1$ and R$_2$ are as defined above or an active functional derivative thereof suitable as an acylating agent for a primary amino group. Such derivatives include the corresponding carboxylic acid chlorides, bromides, acid anhydrides, including mixed anhydrides, prepared from stronger acids such as lower aliphatic monoesters of carbonic acid, or alkyl and aryl sulfonic acids and of more sterically hindered acids such as diphenylacetic acid. Moreover, an acid azide or active thioester (e.g. with thiophenol or thioacetic acid) of the acid may be used.

Alternatively, the free acid itself may be coupled with the 6-aminopenicillanic or 7-aminocephalosporanic acid compound by the use of a carbodiimide reagent. Instead of the 2,4-dinitrophenyl and p-nitrophenyl esters, a corresponding azolide, i.e. an amide of the corresponding acid whose amide nitrogen is a member of a quasiaromatic five membered ring containing at least two nitrogen atoms i.e., imidazole, pyrazole, triazoles, benzimidazole, benazotriazole and their substituted derivatives can be used.

The methods for carrying out these reactions to produce a penicillin or a cephalosporin and the methods used to isolate the compounds so produced are well known in the art such as the British Patents Nos. 932644, 957570, 959054, 952519, 932530, 967108 and 967890.

The ester, salt or amide of the product obtained by the aforesaid processes may be converted by methods known per se into the corresponding penicillanic or cephalosporanic acids. For example, when a silyl (e.g. trialkylsilyl) ester of the starting material of formula IV or V is employed as reactant, the esterifying group can be readily hydrolyzed to yield the corresponding acid compound of formula I.

Another method of the invention for preparing the compounds of general formula I comprises reacting an acid of the formula A-COOH wherein A is the group: a

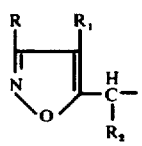

VII in which R, R$_1$ and R$_2$ are as defined above having reactive groups in the radical A suitably protected, with a 6-isocyanatopenicillanic acid or 7-isocyanato-(desacetoxy)cephalosporanic acid compound of the formula O=C=N-Q (wherein Q is as defined above) having atoms or groups protecting the carboxyl group and optional hydroxy group, when present (i.e. when X in formula III is hydroxyl). Preferably the group protecting the carboxyl radical or hydroxy radical when present in the 6-isocyanatopenicillanic or 7-isocyanatocephalosporanic reactant is a di- or tri-alkyl-silyl group which can readily be removed from the resultant product by hydrolysis.

The reaction between the carboxylic acid of formula A-COOH and isocyanate of formula OCN-Q is preferably carried out in an inert organic solvent medium such as toluene, dichloromethane or benzonitrile. A small amount of an organic base, for example a substituted imidazole, may serve as catalyst. The reaction proceeds according to the reaction scheme illustrated below for penicillanic acid derivatives, for example with a protecting ester group:

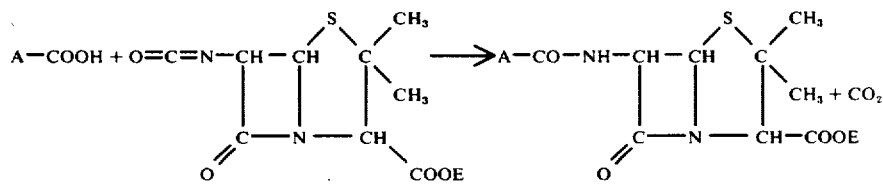

wherein E is a group protecting the carboxyl group during the reaction and is removed, for example by hydrolysis, after the reaction.

In another method for preparing the penicillanic and cephalosporanic acid derivatives of formula I, a 6-isocyanatopenicillanic or 7-isocyanatocephalosporanic acid compound O=C=N—Q wherein Q is as defined above having the carboxyl group, and hydroxy group when present, suitably protected, is reacted with an organo-metal compound of the formula A-Me$^I$, A-Me$^{II}$- Hal or A-Me$^{II}$ -A wherein A is as defined above, Me is a metal atom such as lithium, sodium or magnesium, the numeral I or II indicating its valency, and Hal is a halogen (preferably chlorine or bromine) atom followed by hydrolyzing the intermediate product obtained to remove the metal ion, and any hdyrolyzable group protecting the carboxyl group. The reaction is carried out in an anhydrous organic solvent medium under conditions favoring a reaction of the Grignard, Reformatsky or analogous type.

The isocyanate starting materials of the formula O=C=N—Q wherein Q is as defined above can be prepared by reacting phosgene with a penicillanic or cephalosporanic acid derivative of the formula

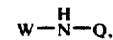

wherein W is hydrogen or a group such that the group W-NH- is easily convertible into an isocyanato group by reaction with phosgene, and the group Q is as defined above with the carboxyl, and hydroxy group when present, suitably protected. The group W in the starting material may be introduced on the amino group of the 6-aminopenicillanic acid or 7-aminocephalosporanic acid derivative concurrently with the protection of the carboxyl group and hydroxyl group or afterwards. Preferably, W is a tri(lower) alkylsilyl group. When W is an easily removable group, the reaction of such compounds with phosgene proceeds much more smoothly under the same reaction conditions than is the case when W is a hydrogen atom. The reaction with phosgene must be carried out in a dry, inert organic solvent medium having regard to the reactivity of the resulting isocyanato groups. Toluene and methylene chloride or mixtures thereof are particularly suitable.

To facilitate the reaction, an organic base can be added to bind the hydrogen chloride formed. Preferably this base is a tertiary amine such as triethylamine which does not react with the isocyanato function. As high temperatures would lead to decomposition of the penicillanic acid or cephalosporanic acid nucleus, the reaction is preferably carried out at very low temperatures, preferably −40° C.

The substituted isoxazol-5-yl acetic acid starting materials of formula VI, most of which are new and thus form an additional feature of the invention, were prepared by the following processes:

ried out in aprotic solvents such as toluene or tetrahydrofuran. Route 1 enables the greatest variation in the desired compounds. In some cases, the group $R_1$ has been changed into another group, e.g. —COOH into —$CONH_2$ or —CN or —$NH_2$, after the 1,3-dipolar addition reaction, but before the lithiation in order to avoid the synthesis of the starting acetylenes which are sometimes difficult to prepare. The introduction of a group $R_2 \neq H$ in formula $VI_A$ can be carried out directly via route 1 by starting with 1-butyne ($R_2=CH_3$) instead of propyne.

The other processes comprise (1) α-halogenation of compounds of formula $VI_A$ optionally followed by reaction with a nucleophilic agent, e.g. α-amino acid (formula VI R=2,6-dichlorophenyl, $R_1$=H, $r_2$=$NH_2$) was prepared via α-bromination of the corresponding methyl isoxazol-5-yl-acetate with 1,3-dibromo-5,5-dimethylhydantoin followed by hydrolysis and reaction of the α-bromo acid with concentrated ammonia. This was an improved synthesis analogus to that one of ibo-

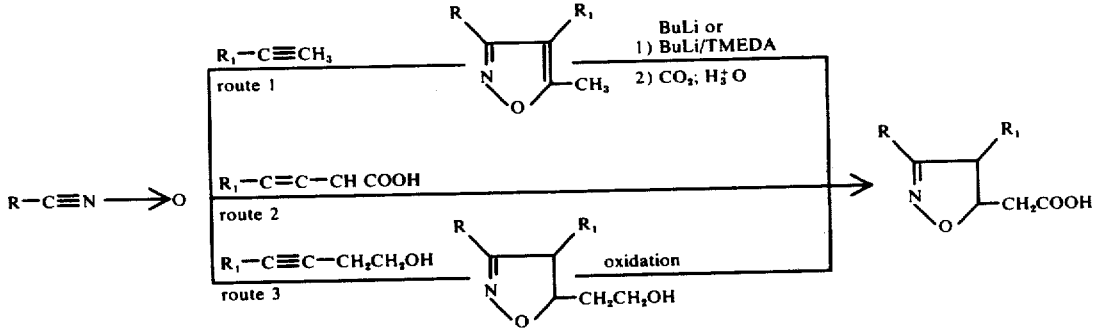

VI A

The starting nitrile oxides can be prepared by known methods; as described by Grundmann, Quilico et al., See e.g. Synthesis 1970, 344 and references cited herein. The reaction with n-butyllithium in the presence of tetramethyleendiamine (TMEDA) can be carried out in aprotic solvents such as toluene or tetrahydrofuran. tenic acid as described in Chem. Pharm. Bull. 14, 89 (1966) and 2) via α-lithiation of the carboxylic acids of formula $VI_A$ and reaction with an appropriate agent. Examples of new compounds of formula VI which can be prepared by the depicted scheme are those, wherein:

| R | $R_1$ | $R_2$ |
|---|---|---|
| Adamantyl | H | H |
| 4-nitrophenyl | H | H |
| 4-aminophenyl | H | H |
| 2,6-dichlorophenyl | H | —NH—C(=O)—O—$CH_2$—C$_6$H$_4$—$NO_2$ |
| 2,6-dichlorophenyl | Cl | H |
| 2,6-dichlorophenyl | $NH_2$ | H |
| 2,6-dichlorophenyl | H | Br |
| 2,6-dichlorophenyl | —C(=O)—$NH_2$ | H |
| 2,6-dichlorophenyl | —C≡N | H |
| 2,6-dichlorophenyl | H | $NH_2$ |
| 2,6-dichlorophenyl | $CH_3$ | H |
| 2,4,6-trimethylphenyl | H | Cl |
| 2,4,6-trimethylphenyl | H | $CH_3$ |

| R | R₁ | R₂ |
|---|---|---|
| 2,4,6-trimethylphenyl | CH₃ | H |

The new penicillanic and cephalosporanic acid derivatives of formula I have antibiotic properties which make them useful with human beings and animals alone or mixed with other known antibiotics. Some of the new compounds of formula I have activities comparable to those of penicillin G and they have special activities against gram positive organism and have, moreover, a good activity against penicillin resistant Staphylococci, especially the compounds in which R represents a methyl or 2,6-dichlorophenyl group, $R_1$ is hydrogen or methyl, $R_2$ is hydrogen and Q is the group of formula II or III in which X represents an acetoxy group, and salts of such compounds.

The compounds according to the invention are preferably employed for therapeutic purposes in the form of a non-toxic pharmaceutically acceptable salt such as the sodium, potassium or calcium salt. Other salts that may be used include the non-toxic, suitably crystaline salts with organic bases such as amines, for example tri(lower)alkylamines, procaine and dibenzylamine.

The novel antibacterial compositions of the invention are comprised of a bactericidally effective amount of a compound of formula I and a pharmaceutical carrier. The said compositions may be in the form of liquid preparation such as solutions, suspensions, dispersions or emulsions or in solid form such as powders, capsules or tablets. One or more other therapeutics may be added to the said compositions.

The term "effective amount" as used herein in relation to the described compounds means an amount which is sufficient to destroy or inhibit the growth of susceptible microorganism when administered in the usual manner or an amount which is sufficient to control the growth of bacteria. The magnitude of an effective amount can be easily determined by those in the art through standard procedures for determining the relative activity of antibacterial agents, when utilized against susceptible organisms via the various available routs of administration.

Suitable carriers and excipients may be any convenient physiologically acceptable ingredient which can serve to facilitate administration of the therapeutically active compound. Carriers may provide some ancillary function such as that of a diluent, flavor-masking agent, binding agent, action delaying agent, stabilizer, and the like. Illustrative carriers include water which can contain gelatin, acacia, algenate, dextran, polyvinylpyrrolidine, sodium carboxymethyl cellulose, or the like, aqueous ethanol, syrup, isotonic saline, isotonic glucose, starch, lactose, or any other such material commonly used in the pharmaceutical and veterinary industry.

The novel method of killing bacteria comprises contacting bacteria with a bactericidal amount of a compound of formula I. When administered to warm-blooded animals, inclusive human beings, the compounds may be administered for example topically or parenterally. The usual daily dose is 5 to 100 mg/kg depending upon the method of administration and the specific compound.

In the following examples these are described several preferred embodiments to illustrate the invention. However, it should be understood that the invention is not intended to be limited to the specific embodiments.

EXAMPLE I

Sodium salt of 6-{[3-(2,6-dichlorophenyl)isoxazol-5-yl]acetamido}-penicillanic acid

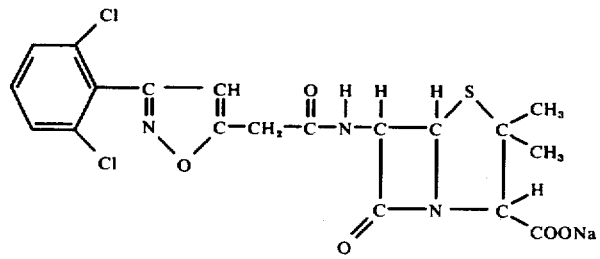

In a three-necked flask equipped with a gas inlet tube, thermometer and dropping funnel, 755 mg (3.5 mmoles) of 6-aminopenicillanic acid were suspended in 10 ml of ethyl acetate under an atmosphere of nitrogen and the flask was cooled in an ice bath while 0.51 ml (3.8 mmoles) of triethylamine were added followed after 10 minutes by 0.48 ml (3.8 mmoles) of trimethylchlorosilane. Stirring was continued for about 35 minutes and then another 0.51 ml (3.8 mmoles) of triethylamine were added followed by 3-(2,6-dichlorophenyl)isoxazol-5-ylacetyl chloride (prepared by the reaction of thionyl chloride with 3-(2,6-dichlorophenyl)isoxazol-5-ylacetic acid in diethyl ether with a trace of dimethylformamide) in 5 ml of ethyl acetate added drop-wise to the reaction mixture at such a rate that the temperature did not rise above 5° C. After the addition, the ice bath was removed and stirring was continued for another 90 minutes at room temperature.

The reaction mixture was then poured into a mixture of 20 ml of water and 20 ml of diethyl ether with ice-cooling, the pH being maintained at 6.8. The aqueous layer was washed again with 30 ml of diethyl ether and the aqueous layer was acidified to pH 1.5 after addition of 40 ml of diethyl ether. After separation, the aqueous layer was washed again with 30 ml of diethyl ether and the combined organic layers were washed once with 20 ml of acidified ice-water at pH 1.5 and then with 20 ml of ice-water. After drying and treatment with Norit, the organic layer was concentrated to about half its volume and then sodium α-ethyl-capronate was added. The precipitated sodium salt is filtered off, washed with diethyl either and dried to obtain 550 mg (32% yield) of the sodium salt of 6-[(3-[2,6-dichlorophenyl] isoxazol-5-yl)acetamido]-penicillanic acid. According to TLC the compound was pure.

EXAMPLE II

Sodium salt of 6-{[3-(2,6-dichlorophenyl)isoxazole-5-yl]acetamido}-penicillanic acid A three-necked vessel of 250 ml was equipped with a thermometer, a good condenser and dropping funnel and the reaction was carried out under nitrogen. 220 ml of dichloromethane and 2.72 g (10mmol) of 3-(2,6-dichlorophenyl)isoxazol-5-ylacetic acid were introduced into the vessel. After the introduction of 0.13 ml of N-vinylimidazole (a catalyst), a solution of 3.14 g (10 mmol) of trimethylsilyl 6-isocyanatopenicillanate in dichloromethane was added drop-wise to the stirred solution at 20° C. After 23 hours, the reaction was complete and the isocyanate was converted to the extent of about 70% into the desired product. The reaction mixture was poured into ice-water buffered to pH 7 and was extracted twice with diethyl ether. The aqueous layer was acidified to pH 4.0 and was extracted three times with diethyl ether. The desired product was completely removed from the aqueous layer and the collected organic layers were washed with a small amount of ice-water and then dried over anhydrous magnesium sulfate, filtered and concentrated to some extent in vacuo at 0° C.

A solution of sodium α-ethylcapronate in ethyl acetate was added drop-wise to the concentrated solution and the resulting colorless precipitate was collected on a filter, washed with diethyl ether and dried in vacuo to obtain 2.81 g (57% yield) of the sodium salt of 6-{[3-(2,6-dichlorophenyl)isoxazole-5-yl]acetamido}-penicillanic acid. Analysis of the PMR spectrum of the product dissolved in hexadeuterodimethylsulphoxide (60 Mc, δ-values in ppm, internal reference tetramethylsilane):

| | |
|---|---|
| NH | doublet at 8.95 (0.7 protons) |
| C₆H₃ | about 7.5 (3 protons) |
| isoxazolyl—H | 6.50 (proton) |
| CH₂— and C₂—H | 3.99 (3 protons) |
| C₅—H and C₆—H | multiplet between 5.50 and 5.30 (2 protons) |
| C₃—(CH₃)₂ | 1.62 and 1.52 (doublet 6 protons) |

Partial analysis of the IR spectrum (in KBr disc, values in cm⁻¹)

| | |
|---|---|
| 3355 | NH |
| 1755 | C = O — lactam |
| 1700 | C = O amide |
| 1610 | C = O carboxylate ion |
| 1505 | NH deformation |
| 1600 | C = C aromatic |
| 1430 | isoxazolyl ring |
| 788 755 | C — Cl stretching vibration |

EXAMPLE III

Sodium salt of 7-{[3-(2,6-dichlorophenyl)-isoxazol-5-yl]acetamido}cephalosporanic acid

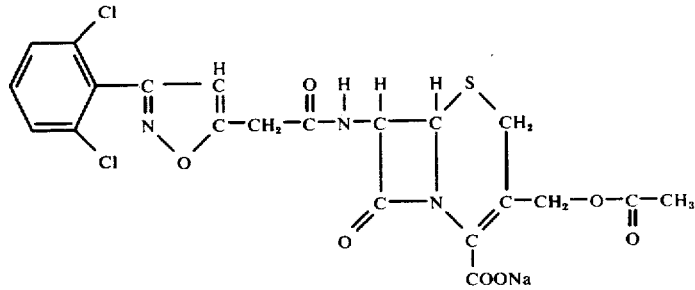

500 mg (1.8 mmol) of 7-aminocephalosporanic acid were suspended in a three-necked vessel, equipped with a gas inlet tube, a thermometer and a dropping funnel, in 10 ml of ethyl acetate under an atmosphere of nitrogen. The suspension was cooled in an ice-bath and 0.3 ml (2.2 mmoles) of triethylamine was introduced. After 5 minutes, 0.3 ml (2.2 mmoles) of trimethylchlorosilane was added to the mixture and stirring was continued for one hour at room temperature. The mixture was cooled again and, after addition of another equivalent of triethylamine, 3-(2,6-dichlorophenyl)isoxazol-5-ylacetyl chloride (prepared as described in Example I) in 5 ml of ethyl acetate was added drop-wise to the reaction mixture with the temperature being maintained below 5° C.

After the addition, the ice-bath was removed and the reaction mixture was stirred for another two hours at room temperature. Then it was poured into a mixture of 30 ml of water and 30 ml of diethyl ether with ice cooling while the pH was kept at 7.0. The aqueous layer was washed with another portion of diethyl ether (30 ml) and ethyl acetate (30 ml). After addition of 50 ml of ethyl acetate, the aqueous layer was acidified to pH 1.7 and the layers were separated and the aqueous layer was extracted again with 50 ml of ethyl acetate. The combined ethyl acetate layers were washed once with acidified ice-water, at pH 1.5 and twice with ice-water. After separation, drying over magnesium sulfate and treatment with Norit, the ethyl acetate layer was concentrated to about one third of its volume and then sodium -ethylcapronate was added. The precipitated sodium salt was washed once with ethyl acetate and twice with n-hexane and after filtration dried in vacuo to obtain 438 mg (0.8 mmoles = 44%) of the sodium salt of 7-[3-(2,6-dichlorophenyl)-isoxazole-5-yl]-acetamido-cephalosporanic acid. According to TLC, the compound was pure.

A partial analysis of the IR-analysis of the final product (KBr disc, values in cm$^{-1}$)

| | |
|---|---|
| ± 3430 } | NH |
| ± 3280 | |
| 1760 | C = Oβ-lactam and C = O ester |
| 1690 – 1670 | C = O amide |
| 1600 | C = O carboxylate ion |
| 1558 | C = C or C = N |
| 1230 } | C — O — C ester |
| 1025 | |
| 782 | C — Cl |

Analysis of the PMR spectrum of the final product dissolved in hexadeuterodimethylsulphoxide (60 Mc, δ-values in ppm, tetramethylsilane as an internal standard).

| | |
|---|---|
| CO —CH$_3$ | 2.3 |
| S —CH$_2$ | 3.07 ⟶ 3.71 AB-quartet (J≈17.5 cps, 2 protons) |
| CH$_2$—C(=O) | 3.98 (2 protons) |
| O—CH$_2$ | 4.73 – 5.20 quartet (J≈12 cps, 2 protons) |
| C$_6$—H | 4.98 and 5.05 doublet (J≈4.5 cps, 1 proton) |
| C$_7$—H | 5.47 ⟶ 5.66 quartet (J≈4.5 cps, J'≈ 8 cps, 1 proton) |
| isoxazol—C$_4$—H | 6.51 (1 proton) |
| C$_6$H$_3$ | 7.55 sharp narrow (3 protons) splitting pattern |
| NH | 9.22 and 9.35 doublet (J'≈8 cps, 1 proton) |

| | Found | Average | Calculated (with 1/2 mole of crystalwater) |
|---|---|---|---|
| C | 44.97 – 45.10 % | 45.03 % | 45.26 % |
| H | 3.31 – 3.38 % | 3.34 % | 3.08 % |
| N | 7.70 – 7.72 % | 7.71 % | 7.54 % |
| S | 5.70 – 5.67 % | 5.68 % | 5.75 % |

EXAMPLE IV

Sodium salt of 7-{[3-2,6-dichlorophenyl)isoxazol-5-yl]acetamido}desacetoxycephalosporanic acid

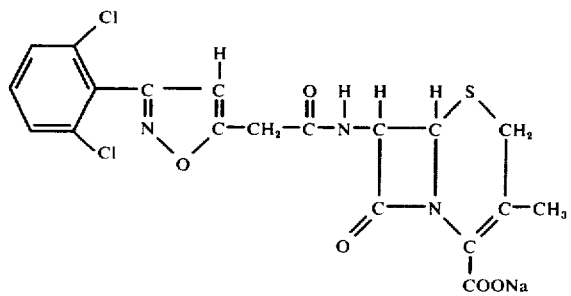

0.46 ml (3.3 mmoles) of triethylamine were added to a suspension of 620 mg (2.9 mmoles) of 7-aminodesacetoxycephalosporanic acid in 10 ml of ethyl acetate in a 50 ml three-necked vessel, equipped with a gas inlet tube, a thermometer and a dropping funnel, under a nitrogen atmosphere and stirred mechanically, after cooling of the suspension with an ice-bath. After 5 minutes, 0.42 ml (3.3 mmoles) of trimethylchlorosilane was introduced and stirring was continued for one hour without external cooling. Then the reaction mixture was cooled again with ice-bath and another 0.41 ml (2.9 mmoles) of triethylamine was added. 3-(2,6-dichlorophenyl)isoxazol-5-ylacetyl chloride (prepared as described in Example I) in 5 ml of ethyl acetate was introduced drop-wise to the reaction mixture at such a rate that the temperature did not rise above 5° C. The cooling bath was removed and stirring was continued for another 2 hours.

The reaction mixture was then poured into a mixture of 20 ml of water and 20 ml of diethyl ether with ice-cooling and mechanical stirring while the pH was maintained at 7.0. The aqueous layer was washed once with 20 ml of ethyl acetate and once with diethyl ether (20 ml). After addition of 40 ml of ethyl acetate to the aqueous layer, the pH was brought to 1.7. The aqueous layer was extracted once again with 30 ml of ethyl acetate and then these layers were combined and washed once with 20 ml of acidified ice-water (pH 1.7) and once with normal ice-water (20 ml). After drying over magnesium sulfate and treatment with Norit, the organic layer was concentrated to about one third of its original volume. Sodium α-ethylcapronate was added and the precipitated sodium salt was collected on a filter, washed with ethyl acetate and with diethyl ether and dried in vacuo to obtain 0.603 mg (1.23 mmoles = 43%) of the sodium salt of 7-[3-(2,6-dichlorophenyl)isoxazol-5-yl]-acetamido desacetoxycephalosporanic acid. According to TLC, the compound was pure.

A partial analysis of the IR spectrum of the final product (KBr disc, values in cm$^{-1}$).

| | |
|---|---|
| ± 3400 | NH (broad absorption) |
| 1750 | C = O β—lactam |
| 1670 | C = O amide |
| 1590 | C = O carboxylate ion |
| 1555 | C = C |
| ± 1540 | NH def. (shoulder) |
| 781 | C—Cl |

Analysis of the PMR spectrum of the final product dissolved in hexadeuterodimethylsulphoxide (60 Mc, δ-values in ppm, tetramethylsilane as an internal standard).

| | | |
|---|---|---|
| $C_3$—$CH_3$ | 1.98 | (3 protons) |
| S—$CH_2$ | 2.95 →3.65 | AB-quartet (J≈17.5 cps; 2 protons) |
| $\overset{O}{\underset{\|}{CH_2C}}$ | 3.98 | (2 protons) |
| $C_6$—H and $C_7$—H | 4.88, 4.97 and 5.43–5.52 | (J≈4.5 cps; 2 protons) |
| isoxazol—$C_4$—H | 6.50 | (1 proton) |
| $C_6H_3$ | 7.55 | sharp narrow (3 protons) splitting pattern |

EXAMPLE V

6-{[3-(2,6-dichlorophenyl)-4-carboxyisoxazol-5-yl]acetamido}penicillanic acid

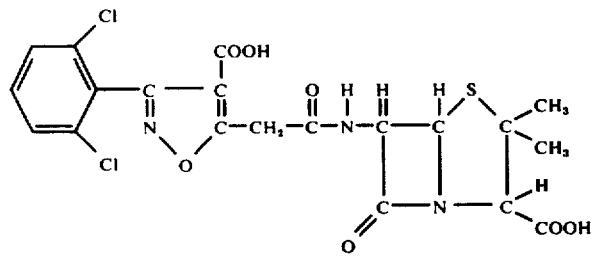

In a three-necked flask equipped with a gas inlet tube, thermometer and dropping funnel, 314 mg (1.0 mmoles) of trimethylsilyl 6-isocyanatopenicillanate and 316 mg (1.0 mmoles) of 3-(2,6-dichlorophenyl)-4-carboxyisoxazol-5-ylacetic acid (prepared by the reaction of 3-(2,6-dichlorophenyl)-4-carboxy-5-methylisoxazole formed via a 1,3-dipolar addition of 2,6-dichlorophenyl benzonitriloxide and trimethylsilyl 2-butynoate with 2 equivalents of n-butyl lithium and one equivalent of tetramethylethylenediamine in toluene followed by carboxylation with $CO_2$) were dissolved in 25 ml of benzonitrile. To this mixture, a solution of 145 mg (1.1 mmoles) of N-methylbenzimidazole in 5 ml of benzonitrile was added dropwise and there was a direct formation of carbon dioxide. After two hours, the carbon dioxide evolution ceased, and the reaction mixture was then poured into a mixture of 30 ml of water and 50 ml of diethyl ether with ice-cooling, the pH being maintained at 7. The aqueous layer was extracted twice more with 50 ml of diethyl ether.

After addition of 50 ml of diethyl ether and 10 ml of ethyl acetate, the pH was brought to 4. The layers were separated and the aqueous layer was extracted twice with 50 ml of diethyl ether. The combined organic layers were washed with ice-water and dried over magnesium sulfate. After removal of the solvent, 136 mg of a slightly yellow solid was left behind, which was pure 6-[3-(2,6-dichlorophenyl)-4-carboxyisoxazol-5-yl]acetamido penicillanic acid according to TLC.

A partial analysis of the IR spectrum of the final product (KBr disc, values in $cm^{-1}$).

| | |
|---|---|
| 1775 | C = O β—lactam |
| 1700 | C = O carboxyl |
| 1600 | C = C aromatic |
| 1560 | C = N |
| 1430 | isoxazole ring |
| 780 | C — Cl |

Analysis of the PMR spectrum of the final product dissolved in hexadeuterodimethylsulphoxide (60 Mc, δ-values in ppm, tetramethylsilane as an internal standard).

| | |
|---|---|
| $C_3$—$CH_3$ | 1.52 and 1.65 (6 protons) |
| $\overset{O}{\underset{\|}{CH_2C}}$ and $C_2$—H | 4.32 (3 protons) |
| $C_5$—H and $C_6$—H | 5.33 →5.70 multiplet (2 protons) |
| $C_6H_3$ | 7.55 sharp narrow splitting pattern |
| NH | 9.10 doublet |

EXAMPLE VI

Sodium salt of 6-{[3-(2,4,6-trimethyl)phenylisoxazol-5-yl]acetamido}penicillanic acid.

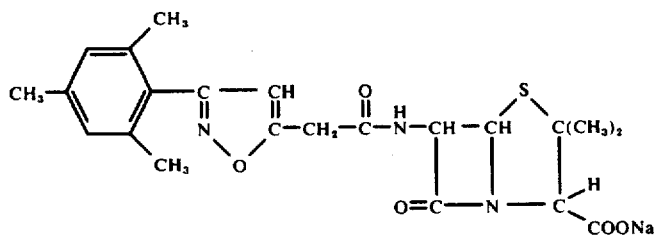

Using the procedure of Example II, 1.23 g (5 mmol) of 3-(2,4,6-trimethyl)-phenyl-isoxazol-5-yl-acetic acid were reacted with 1.57 g (5 mmol) of trimethylsilyl 6-isocyanato-penicillanate in 25 ml of dry dichloromethane in the presence of about 0.05 ml of N-vinylimidazole (catalyst). The reaction was finished after 6.5 hours and according to thin-layer chromatography, the isocyanate was converted into the desired product to the extent of about 60%. The reaction product was treated in the usual fashion. At pH 4.5, the penicillin was extracted from water with diethyl ether and the solution in ether was washed with a small volume of ice-water, treated with activated charcoal, dried over anhydrous magnesium sulfate and concentrated in vacuo to some extent at 0° C.

A solution of sodium α-ethylcapronate in diethyl ether was added drop-wise to the concentrated solution and the colorless precipitate formed was recovered by filtration and washed repeatedly with cold diethyl ether. After drying in vacuo, the product, sodium salt of 6- [3-(2,4,6-trimethyl)phenylisoxazol-5-yl]acetamido -penicillanic acid, weighed 0.8 g. Good purity of the product was indicated by thin-layer chromatography, IR and PMR spectra. Analysis of the PMR spectrum of the final product dissolved in a about 2:1 mixture of hexadeuterodimethylsulphoxide and $D_2O$ (60 Mc,δ-values in ppm, internal reference 2,2-dimethylsilapentane-5-sulphonate):

| | |
|---|---|
| $C_6H_2$ | 6.95 (singlet, 2 protons) |
| isoxazolyl $C_4H$ | 6.3 (1 proton) |
| $C_5$—H and $C_6$—H | about 5.45 (AB-quartet, $\gamma_{AB}$ <0,1 ppm, $J_{AB} \approx$ 4 cps, 2 protons) |
| $C_2$—H | 4.2 (1 proton) |
| $CH_2$—CO— | 3.95 (2 protons) |
| p-$CH_3$ | 2.25 (3 protons) |
| (o-$CH_3$)$_2$ | 2.05 (6 protons) |
| $C_3$-($CH_3$)$_2$ | 1.5 and 1.6 (6 protons) |

EXAMPLE VII

Sodium salt of 7-{[3-(2,4,6-trimethyl)phenylisoxazol-5-yl]acetamido}cephalosporanic acid.

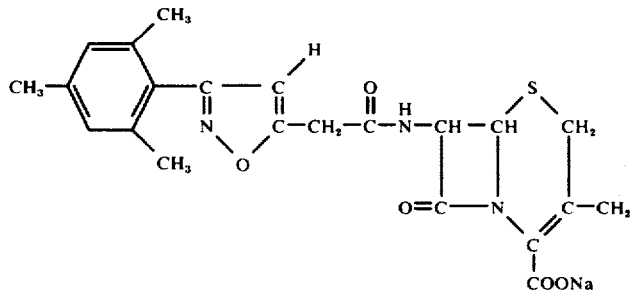

2.8 ml (20 mmol) of triethylamine were added dropwise to a stirred suspension of 2.7 g (10 mmol) of 7-amino-cephalosporanic acid in 40 ml of dry dichloromethane at 0° C. Next, 2.55 ml (20 mmol) of trimethylchlorosilane were added drop-wise and after completion of the addition, the reaction mixture was held a few minutes at 0° C followed by removal of the icebath. Stirring was continued for 1 hour at room temperature. subsequently, 1.2 ml (10 mmol) of quinoline were added, followed by the drop-wise introduction of a solution of approximately 10 mmol of 3-(2,4,6-trimethyl)phenylisoxazol-5-yl-acetyl chloride in 20 ml of dry dichloromethane at 5° C. After a few minutes additional stirring at room temperature, the reaction mixture was poured into ice water followed by addition of dilute sodium hydroxide. At pH 7 the layers were separated and the water-layer twice was extracted with diethyl ether. The organic layers were discarded and the water-layer between pH 5 and pH 1 was repeatedly extracted with diethyl ether. The organic layers were separately inspected by thin-layer chromatography. The cleanest extracts were combined, washed with ice water, dried over anhydrous magnesium sulfate, filtered, concentrated somewhat in vacuo and finally treated with a solution of sodium α-ethylcapronate in ether. The solid precipitate was collected by filtration, washed with diethyl ether and dried in vacuo to constant weight to obtain 2.5 g of the sodium salt of 7-[3-(2,4,6-trimethyl)phenylisoxazol-5-yl]-acetamido-cephalosporanic acid. In order to obtain the crystalline monohydrate, the crude product which according to thin-layer chromatography did not contain other sulphur containing substances was crystallized from acetone. The final produce (1 g) was pure except for the presence of a small amount of acetone, and it contained one mole of water per mole of water per mole of cephalosporin. Analysis of the PMR spectrum of the final product dissolved in hexadeutero-dimethylsulphoxide (60 Mcδ-values in ppm, internal reference 2.2-dimethyl-silapentane-5-sulphonate):

| | |
|---|---|
| N—H | 9.26 and 9.12 (doublet, J≈8.5 cps, about 0.8 proton) |
| $C_6H_2$ | 6.93 (slightly broadened singlet, 2 protons) |
| isoxazolyl—$C_4$—H | 6.33 (singlet, 1 proton) |
| $C_7$—H | 5.66, 5.58, 5.52 and 5.44 (slightly broadened signals, J≈8.5 cps and $J_{AB}$≈4.7 cps, 1 proton) |
| $C_6$—H | 5.04 and 4.96 ($J_{AB}$=4.7 cps) ⎫ |
| O—$CH_2$ | 5.20, 4.99, 4.92 and 4.71($J_{AB}$ ⎬ 3 prots. 12.5 cps) ⎭ |
| $CH_2$—CO | 3.92 (broadened singlet, 2 protons) |
| S—$CH_2$ | ~3.72, ~3.43, ~3.33 and ~3.04 (broadened signals, AB-quartet, $J_{AB}$≈17.5 cps, 2 protons) |
| p—$CH_3$ | 2.27 (3 protons) ⎫ |
| (o-$CH_3$)$_2$ | 2.07 (singlet) ⎬ 9 protons |
| O—CO—$CH_3$ | 2.01 (singlet) ⎭ |

EXAMPLE VIII

7-{[3-(2,6-dichloro)phenyl-4-methyl-isoxazol-5-yl]acetamido desacetoxycephalosporanic} acid.

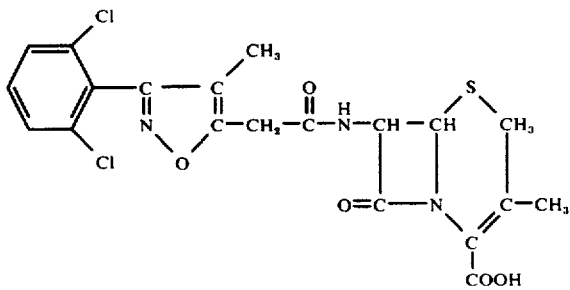

A solution of approximately 1 mmol of trimethylsilyl 7-isocyanato-desacetoxycephalosporanate in 2 ml of toluene was added to 286 mg (1 mmol) of 3-(2,6-dichloro)phenyl-4-methyl-isoxazol-5-yl-acetic acid partly dissolved in 10 ml of dry toluene. Introduction of approximately 0.1 mmol of 1-isopropyl-benzimidazole (catalyst) brought about the onset of a slow reaction (duration about 24 hours at room temperature). When the liberation of carbon dioxide was no longer noticeable in the stream of dry nitrogen passed over the surface of the stirred reaction mixture, the contents of the vessel were poured into a well stirred mixture of iced water and diethyl ether. The pH was brought to 6.8 and the layers were separated and the water-layer was twice extracted with diethyl ether.

The combined organic layers were twice washed with iced water. The organic layer was discarded and the combined water-layers (70 ml) were extracted at pH 2.3 with 80 ml of a 2:1 mixture of diethyl ether and ethylacetate. This extract was twice washed with 5 ml of iced water, dried over anhydrous magnesium sulfate, filtered and completely evaporated in vacuo. The residual, slightly yellow oil solidified when stirred with dry diethyl ether. The ether was decanted and the solid again stirred twice with ether. The almost colorless solid was dried in vacuo to constant weight to obtain 290 mg of 7-{[3-(2,6-dichloro)phenyl-4-methyl-isoxazol-5-yl]acetamido}desacetoxycephalosporanic acid. The final product was examined by thin-layer chromatography which indicated the presence of only one sulphur containing compound. The alleged structure was confirmed by IR and PMR spectra. The PMR spectrum revealed that the final product was about 82% pure since it consisted of 1 mole of the starting acetic acid and 2.5 moles of diethyl ether (probably crystal bound) on 5 moles of the desired product. Partial analysis of the IR spectrum of the final product (in chloroform, values in cm$^{-1}$):

| | |
|---|---|
| ±3500 | OH carboxyl |
| ±3300 | NH |
| 1772 | C=O β—lactam |
| ±1730 | C=O carboxyl |
| 1690 | C=O amide |
| 1380 – 1430 | isoxazole ring absorptions |

EXAMPLE IX

Cyclohexylamine salt of 6-{α-chloro-[3-(2,4,6-trimethyl)phenyl-isoxazol-5-yl]acetamido}penicillanic acid.

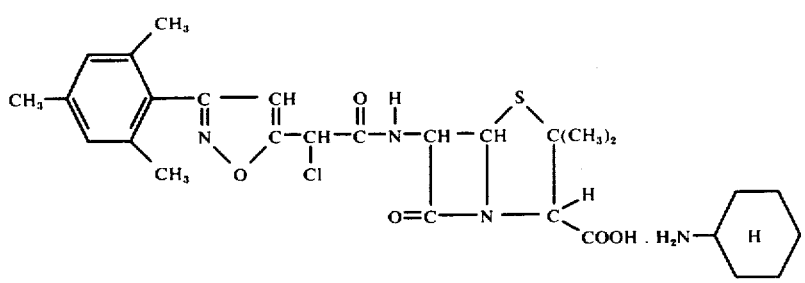

A solution of 700 mg of trimethylsilyl 6-isocyanato-penicillanate in 10 ml of dry dichloromethane was added drop-wise over 25 minutes to a solution of 700 mg of 1-chloro-1-[3-(2,4,6-trimethyl)phenyl-isoxazol-5-yl] acetic acid and about 0.03 ml of N-vinyl-imidazole (catalyst) in 25 ml of dry dichloromethane. The reaction mixture was additionally stirred during 4 hours. In situ hydrolysis of the silylester was achieved by the addition of about 0.2 ml of ethanol at 0° C. The reaction mixture was poured into a well stirred mixture of diethyl ether and iced water buffered to pH 7. After separation of the layers, the water-layer was one more extracted with diethyl ether and subsequently acidified to a pH of 3.5. The desired compound was incompletely removed from the water layer by two extractions with diethyl ether. These extracts were combined, washed with a small volume of iced water, dried over anhydrous magnesium sulfate and evaporated in vacuo. The residual oil was dissolved in 5 ml of acetone and a dilute solution of cyclohexylamine in diethyl ether was added slowly until no further increase of precipitate was noticed. The colorless solid was collected by filtration, washed with cold diethylether and dried in vacuo to obtain 250mg of the cyclohexylamine salt of 6-[α-chloro-[3-(2,4,6-trimethyl)phenylisoxazol-5-yl] acetamido]-penicillanic acid. The identity of the final product was confirmed by PMR spectra and IR spectra (KBr disc, 1775 cm$^{-1}$: C=O β-lactam, 1680 cm$^{-1}$: C=O amide, 1390 and 1450 cm$^{-1}$: isoxazole ring). The purity of the final product was estimated to be about 85%.

EXAMPLE X

Sodium salt of 6-{[3-(2,6-dichloro)phenyl-4-methyl-isoxazol-5-yl]acetamido}penicillanic acid.

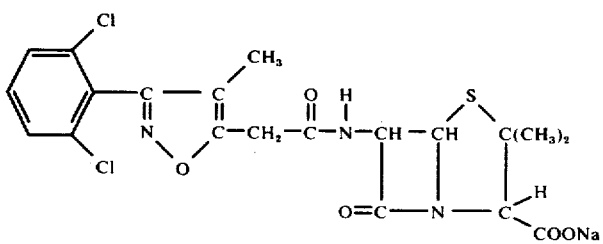

Using the procedure of Example II, 286 mg (1 mmol) of 3-(2,6-dichloro)phenyl-4-methyl-isoxazol-5-yl-acetic acid were reacted with 314 mg (1 mmol) of trimethylsilyl 6-isocyanato-penicillanate in 10 ml of dry toluene in the presence of about 0.01 ml of N-isopropyl-benzimidazole (catalyst).

The reaction of the mixture was stirred over night at about 15° C and according to a thin-layer chromatogram, the isocyanate could have been converted into the desired product for at least 75%. The reaction product was treated in the usual manner. At pH 3.8, the penicillin was removed from the water-layer by three 40 ml extractions with diethyl ether. The combined extracts were washed with iced water, dried over anhydrous magnesium sulfate, filtered and concentrated in vacuo to a volume of about 5 ml. Addition of a solution of sodium α-ethylcapronate in diethyl ether resulted in a colorless precipitate which was recovered by filtration, was washed with cold diethyl ether and dried in vacuo to constant weight. Finally, the product was triturated in a small volume of cold dry acetone to obtain 300 mg the sodium salt of 6-{[3-(2,6-dichloro)-phenyl-4-methyl-isoxazol-5yl]acetamido}-penicillanic acid. Examination of the final product by thin-layer chromatography, IR spectra and PMR spectra confirmed the structure. The product was contaminated with only very small amounts of acetone and sodium α-ethylcapronate. Analysis of the PMR spectrum of the final product dissolved in hexadeuterodimethylsulphoxide (60 Mc,δ-values in ppm, internal reference 2.2-dimethylsilapentane-5-sulphonate):

| | |
|---|---|
| $C_3-(CH_3)_2$ | 1.54 and 1.64 (6 protons) |
| isoxazolyl $C_4-CH_3$ | 1.82 (3 protons) |
| $CH_2-CO-$ | about 3.95 (broadened singlet) (3 protons) |
| $C_2-H$ | 4.03 |
| $C_5-H$ and $C_6-H$ | about 5.5 (multiplet, 2 protons) |
| $C_6-H_3$ | about 7.6 (sharp narrow splitting pattern, 3 protons) |
| $N-H$ | about 9.3 (doublet, 0.9 protons) |

EXAMPLE XI

Cyclohexylamine salt of 6{α-methyl-[3-(2,4,6-trimethyl)phenylisoxazol-5-yl]acetamido}penicillanic acid.

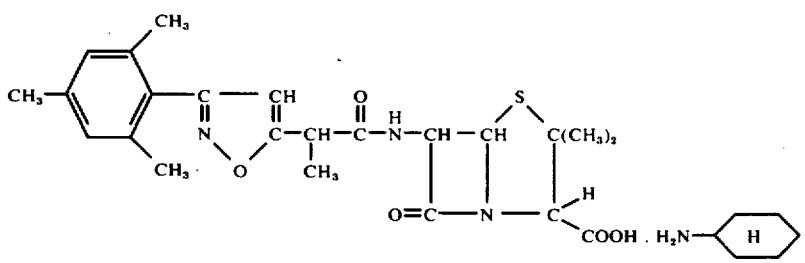

Using the procedure of Example IX, a reaction with equimolar amounts of trimethylsilyl 6-isocyanato penicillanate and 1-methyl-1[3-(2,4,6-trimethyl)phenyl-isoxazol-5-yl]acetic acid was carried out in the presence of a small amount of N-vinyl-imidazole using as solvent, dry dichloromethane. The conversion was completed after 6 hours stirring at room temperature and the reaction mixture was treated in the usual fashion. In the isolation procedure, the penicillin was extracted at pH 4 with diethyl ether and finally obtained as its cyclohexylamine salt. Thin-layer chromatograms, the IR spectrum (insensitive β-lactamcarbonyl absorption at 1778 $cm^{-1}$ (KBr disc) and the PMR spectrum confirmed the structure of the final product and indicated its good state of purity. Partial analysis of the complicated PMR spectrum of the final product (a mixture of the D- and the L-isomer) dissolved in hexadeuterodimethylsulphoxide (60 Mc,δ-values in ppm, internal reference 2.2-dimethyl-silapentane-5-sulphonate):

| | |
|---|---|
| $N-H$ | 8.9 (about 1 proton) |
| $C_6H_2$ | 6.95 (somewhat broadened singlet, 2 protons) |
| isoxazolyl $C_4-H$ | 6.35 (2 close singlets, 1 proton) |
| $C_5-H$ and $C_6-H$ | about 5.4 (2 protons) |
| $C_a-H$ | about 4.2 (diffuse quartet) } 2 protons |

| | |
|---|---|
| $C_2$—H | about 4.0 (2 close singlets) |
| cyclohexyl $C_1$—H | about 2.9 (broad absorption area, about 1 proton) |
| p-CH$_3$ | 2.3 (singlet, about 3 protons) ⎫ |
| (o-CH$_3$)$_2$ | 2.1 (singlet, about 6 protons) ⎬ roughly about 26 prot. |
| cyclohexyl C$_5$H$_{10}$ | about 0.9 → about 2.3 ⎭ |
| $C_3$—(CH$_3$)$_2$ and $C_\alpha$—CH$_3$ | about 1.4 → about 1.65 |

EXAMPLE XII

Sodium salt of 7-{[3-(2,4,6-trimethyl)phenyl-4-methyl-isoxazol-5-yl]acetamido}cephalosporanic acid

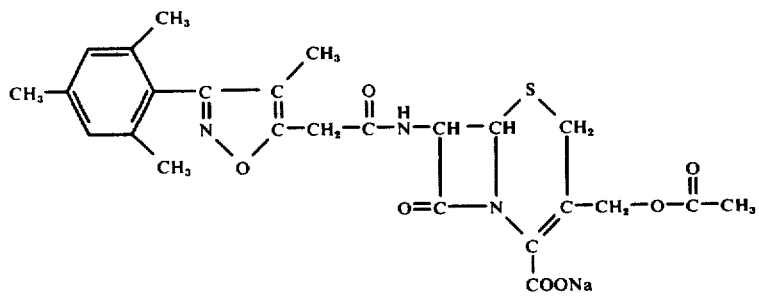

1.38 ml (10 mmol) of triethylamine were added drop-wise to a stirred suspension of 1.3 g (5 mmol) of 7-aminocephalosporanic acid in 20 ml of dry dichloromethane at 0° C. Next, 1.26 ml (10 mmol) of trimethylchlorosilane were added drop-wise at 0° C and after completion of the addition of trimethylchlorosilane, the reaction mixture was stirred for a few minutes at 0° C followed by removal of the ice-bath. Stirring was continued for 1 hour at room temperature and then 0.6 ml (5 mmol) of quinoline were added followed by the drop-wise introduction of a solution of approximately 4.5 mmol of 3-(2,4,6-trimethyl)phenyl-4-methyl-isoxazol-5-yl-acetyl chloride (in about 90% purity prepared from 1.3 g (5 mmol) of the corresponding carboxylic acid) in 10 ml of dry dichloromethane at 5° C. After a few minutes additional stirring at room temperature, the reaction mixture was poured in iced water. The pH was raised to 7 and the layers were separated. The waterlayer, containing according to thin-layer chromatograms one main reaction product, a small amount of 7-amino-cephalosporanic acid and a small amount of a by product (possibly the $\Delta_2$-isomer of the desired product), was washed twice with diethyl ether. The organic layers were discarded and the waterlayer was successively extracted at pH 5.0, 4.5 and 4.0 with diethyl ether. The extract of pH 4.0 contained only the desired main product. Addition of a solution of sodium α-ethylcapronate to this extract gave a colorless solid precipitate for 1.2 g of the sodium salt of 7-{[3-(2,4,6-trimethyl)phenyl-4-methyl-isoxazol-5-yl]acetamido}-cephalosporanic acid. According to thin-layer chromatograms, IR and PMR spectra the final product was only contaminated by small residual amounts of diethyl ether (about 1% by weight). Analysis of the PMR spectrum of the final product dissolved in an about 2:1 mixture of hexadeuterodimethylsulphoxide and D$_2$O (60 Mc,δ-values in ppm, internal reference 2.2-dimethylsilapentane-5-sulphonate):

| | |
|---|---|
| $C_6H_2$ | 6.95 (singlet, 2 protons) |
| $C_7$—H | 5.72 and 5.64 (doublet, J≈4.6 cps, 1 proton) |
| $C_6$—H | 5.10 and 5.02 (doublet, J≈4.6 cps) ⎫ |
| O—CH$_2$ | about 5.15, 4.92, 4.81 and 4.59 ⎬ 3 protons (AB-quartet, J≈13.2 cps) ⎭ |
| S—CH$_2$ | about 3.55 (center of AB quartet) ⎫ 4 protons |
| CH$_2$—CO | 3.87 (somewhat broadened singlet) ⎭ |
| p-CH$_3$ | 2.28 (3 protons) |
| O—CO—CH$_3$ | 2.05 (singlet) ⎫ 9 protons |
| (o-CH$_3$)$_2$ | 1.98 (singlet) ⎭ |
| isoxazolyl—$C_4$—CH$_3$ | 1.71 (3 protons) |

EXAMPLE XIII

Sodium salt of
7-{[3-(2,4,6-trimethyl)phenyl-4-methyl-isox-azol-5-yl]acetamido}desacetoxycephalosporanic acid.

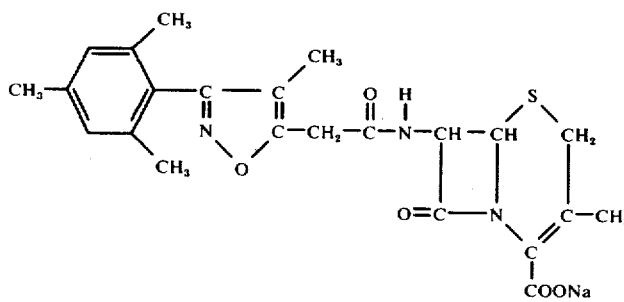

Using the procedure of Example IX, a reaction was carried out between 1.3 g (5 mmol) of 3-(2,4,6-trimethyl) phenyl-4-methyl-isoxazol-5-yl-acetic acid dissolved in 25 ml of dry dichloromethane and 5.04 mmol of trimethylsilyl 7-isocyanato -desacetoxycephalosporanate dissolved in 9 ml of toluene in the presence of about 0.05 ml of N-vinyl-imidazole (catalyst). The addition of the solution of the isocyanate in toluene took about 20 min. Evolution of carbon dioxide was already noticeable after 5 min. and after 7.5 hours additional stirring the reaction was interrupted since a thin-layer chromatogram of the reaction mixture indicated conversion of the isocyanate for about 80% in the desired direction and evolution of carbon dioxide had almost stopped. The reaction mixture was treated in the usual fashion. The cephalosporin was extracted at pH 4.5 with a 9:1 mixture of diethyl ether and ethyl acetate and the combined extracts were washed with iced water, dried over anhydrous magnesium sulfate, filtered and completely evaporated in vacuo. The residual oil was dissolved in diethyl ether. Addition of a part of the estimated necessary amount of sodium α-ethylcapronate dissolved in diethyl ether resulted in a precipitate which was recovered by filtration and was washed with a small amount of cold diethyl ether, and dried in vacuo, Sodium α-ethylcapronate was again added to the combined filtrates. The resulting second crop of solid material was treated like the first crop.

The third and last crop was obtained by adding dissolved sodium α-ethylcapronate till no further increase of precipitate occurred. The third crop being practically pure according to thin-layer chromatography was crystallized from acetone. Finally, the three crops were dissolved together in acetone. The acetone solution was somewhat concentrated in vacuo and subsequently seeded. After crystallization had subsided, the flask was placed in the refrigerator. The next day the crystals were recovered by filtration, were washed with cold acetone and diethyl ether and dried in vacuo to constant weight to obtain 1.7 g of the sodium salt of 7-{[3-(2,4,6-trimethyl)phenyl-4-methyl-isoxazol-5-yl]acetamido}-desacetoxycephalosporanic acid. The structure was confirmed by IR and PMR spectra. According to PMR spectra and thin-layer chromatograms, the final product was contaminated only by a very small amount of acetone and a small amount of N,N'-didesacetoxycephalosporanic acid urea. Analysis of the PMR spectrum of the final product dissolved in an about 2:1 mixture of hexadeuterodimethylsulphoxide and $D_2O$ (60 Mc,δ-values in ppm, internal reference 2.2-dimethylsilapentane-5-sulphonate):

| | |
|---|---|
| $C_6H_2$ | 6.97 (slightly broadened singlet, 2 protons) |
| $C_7$—H and $C_6$—H | 5.63, 5.46, 4.97 and 4.90 (AB-quartet, J≈4.5 cps, 2 protons) |
| $CH_2$—CO | 3.86 (broadened singlet, 2 protons) |
| S—$CH_2$ | about 3.7 —→2.9 (AB-quartet, J≈ 17.5±1 cps, 2 protons) |
| p-$CH_3$ | 2.29 (3 protons) |
| (o-$CH_3$)$_2$ | 1.98 (singlet) ⎫ |
| $C_3$—$CH_3$ | 1.94 (singlet) ⎬ 9 protons |
| isoxazol—$C_4$—$CH_3$ | 1.71 (3 protons) |

EXAMPLE XIV

6-{[3-(2,6-dichloro)phenyl-4-carbamyl-isoxazol-5-yl]acetamido} penicillanic acid

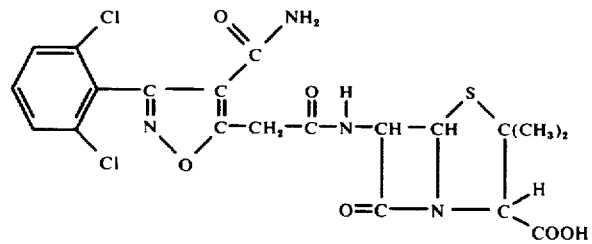

600 mg (2 mmol) of 3-(2,6-dichloro)phenyl-4-carbamyl-isoxazol-5-yl-acetic acid and 630 mg (2 mmol) of trimethylsilyl 6-isocyanato-penicillanate were dissolved in a mixture of 15 ml of dry benzonitrile and 15 ml of dry tetrahydrofuran directly followed by the addition of about 0.02 ml of N-methyl-imidazole.

Evolution of carbon dioxide diminished strongly after three hours stirring at room temperature and a thin-layer chromatogram of the reaction mixture indicated good conversion of the isocyanate. The reaction mixture was poured into a well stirred ice-cold mixture of 30 ml of water, 20 ml of diethyl ether and 20 ml of ethyl acetate. Dilute sodium hydroxide was added till pH 8.5. The layers were separated and the water-layer was purified by extraction with diethyl ether. The organic layers were discarded and the water-layer at pH 3.0 was extracted with a 1:1 mixture of diethyl ether and ethyl acetate. The combined extracts were washed with iced-water, dried over anhydrous magnesium sulfate, filtered and completely evaporated in vacuo. The resulting, slightly yellowish solid (1.1 g) was examined by IR and PMR. The product contained the desired 6-{[3-(2,6-dichloro)phenyl-4-carbamyl-isoxazol-5-yl]acetamido} penicillanic acid and also minor amounts of N,N'-di-penicillanic acid urea and the stirring carboxylic acid. In order to obtain a more pure sample, the crude product was repeatedly extracted with cold-dry diethyl ether in which the urea is slightly soluble. The ethereal extract was mixed with iced water buffered to pH 7 and the greater part of the starting carboxylic acid was removed from the water-layer at pH 4.5. Finally, the water-layer was repeatedly extracted at between pH 4.5 and pH 3.5 with mixtures of much diethyl ether and small but gradually increased amounts of ethyl acetate. Extracts free from the starting carboxylic acid, the urea and degradation products were combined and after the usual manipulations were completely evaporated in vacuo. The resulting colorless solid was dried to constant weight to obtain 350 mg of product. According to thin-layer chromatograms, IR and PMR spectra the final product was pure except for the presence of slight residual amounts of ethyl acetate and diethyl ether. The IR spectrum (KBr disc), complicated by the monomer-dimer feature, i.a. showed a broad intensive area between 3000 and 3600 cm⁻¹ with peaks at 3450, 3350 and 3200 cm⁻¹ ascribable to NH absorptions of both amide groups, a carboxyl OH absorption at about 2550 cm⁻¹, a broad very intensive carbonyl absorption area with peaks at ± 1790, ± 1725, ± 1695 and ± 1655 cm⁻¹ ascribable respectively to the β-lactam, the carboxyl, the CO.NH and the CO.NH₂ group.

EXAMPLE XV

Sodium salt of 6-{[3-(2,6-dichloro)phenyl-4-cyano-isoxazol-5-yl]acetamido}penicillanic acid

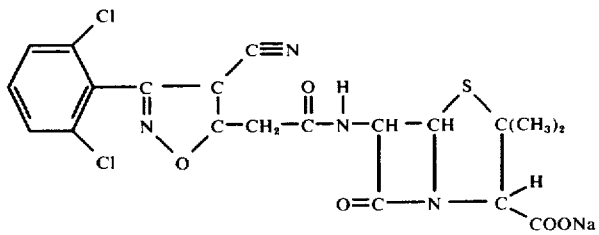

297 mg (1 mmol) of 3-(2,6-dichloro)phenyl-4-cyano-isoxazol-5-yl-acetic acid, 314 mg (1 mmol) of trimethylsilyl 6-isocyanato-penicillanate and a trace of N-isopropylbenzimidazole were dissolved in 5 ml of dry dichloromethane. According to a thin-layer chromatogram, good conversion of the isocyanate was reached after 3 hours reaction at room temperature and then the reaction product was treated in the usual fashion. In the isolation procedure, the solution of the penicillin in water was purified by extractions with diethyl ether at pH 7.0 and 4.5. The penicillin was removed from water by extraction with diethyl ether at pH 3.3 and the ethereal extract was washed with iced water, dried over anhydrous magnesium sulfate, filtered and evaporated in vacuo. The residual oil was dissolved in about 3 ml of dry ethyl acetate followed by the addition of about 0.6 mmol of sodium α-ethylcapronate dissolved in a small volume of ethyl acetate. Addition of dry diethyl ether resulted in a slightly colored precipitate which was recovered by filtration, was washed with cold diethyl ether and dried in vacuo to constant weight to obtain 180 mg. The final product was examined as usual and it contained the sodium salt of 6-{[3-(2,6-dichloro)phenyl-4-cyanoisoxazol-5-yl]acetamido}penicillanic acid and slight amounts of a degradation product and of sodium α-ethylcapronate. The IR spectrum of the final product (KBr disc) exhibited i.a. absorptions at 2280 (C ≡ N), 1778 (carbonyl β-lactam), 1690 (carbonyl amide), 1610 (carbonyl carboyxlate ion) and ± 1400 cm⁻¹ (isoxazole ring absorptions).

EXAMPLE XVI

Sodium salt of 6-{[3-(1)adamantyl-isoxazol-5-yl]acetamido} penicillanic acid

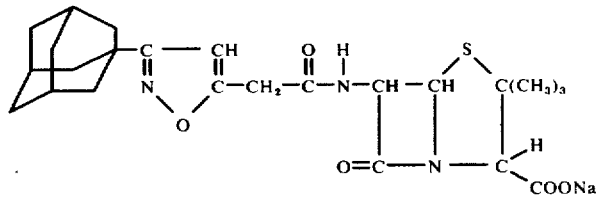

Using the procedure of Example IX, a solution of 780 mg (2.5 mmol) of trimethylsilyl 6-isocyanato-penicillanate in 10 ml of dry dichloromethane was added dropwise to a solution of 650 mg (2.5 mmol) of 3-(1)-adamantyl-isoxazol-5-yl-acetic acid and about 0.02 ml of N-vinyl-imidazole in 20 ml of dry dichloromethane. The conversion was finished after a total of 2.5 hours stirring at room temperature as indicated by a drastic diminshment of evolution of carbon dioxide. A thin-layer chromatogram indicated good conversion of the isocyanate into the desired penicillin and the reaction product was treated as usual. In the isolation procedure, the penicillin was extracted from water by two extractions with diethyl ether, one performed at pH 5.5 and the other at pH 4.0. The extracts were separatedly washed with iced water, dried over anhydrous magnesium sulfate, filtered and completely evaporated in vacuo to obtain yields of 700 and 300 mg, respectively. Both products gave satisfactory IR spectra and contained according to thin-layer chromatography only one penicillin. Since the sample obtained by extraction at pH 5.5 was contaminated by the starting acetic acid derivative, it was dissolved in ether followed by addition of sodium α-ethylcapronate. The obtained sodium salt (350 mg) of 6-{[3-(1)adamantyl-isoxazol-5-yl]acetamido}penicillanic acid was pure except for a slight amount of residual sodium α-ethylcapronate. According to a PMR spectrum the second product was pure except for a slight amount of diethyl ether (about 4.0% by weight). Partial analysis of the IR spectrum of the sodium salt of the final product (KBr disc, values in cm$^{-1}$):

| ±3400 | NH | 1605 C=O carboxylate ion |
| 2910 | | ±1520 NH def. |
| 2853 | CH$_2$ groups | ±1405 isoxazole ring absorption |
| 1775 | C=O β-lactam | |
| ±1675 | C=O amide | |

Analysis of the PMR spectrum of the final product (the acid) dissolved in hexadeuterodimethylsulphoxide (60 Mc, δ-values in ppm, internal reference 2.2-dimethyl-silapentane-5-sulphonate):

EXAMPLE XVII

6-{α-p-nitro-benzyloxycarbonylamino-[3-(2,6-dichloro)phenylisoxazol-5-yl] acetamido}penicillanic acid

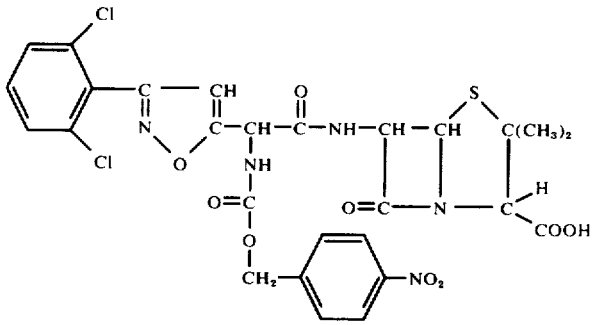

2.33 g (5 mmol) of 1-(p-nitro)benzyloxycarbonylamino-1-[3-(2,6-dichloro)phenyl-isoxazol-5-yl]acetic acid, 1.57 g (5 mmol) of trimethylsilyl 6-isocyanato-penicillanate and 0.1 ml of N-vinyl-imidazole (catalyst) were dissolved in 50 ml of dry dichloromethane. After 3 hours stirring under nitrogen at room temperature, the conversion was completed and according to thin-layer chromatography, the isocyanate could have been converted for about 70% into the desired product. The reaction product was cooled down to 0° C followed by the addition of a few ml of cold acetone containing enough water to hydrolyze the silylester. Next, the mixture was completely evaporated in vacuo in the cold and the residue was dissolved in 75 ml of a cold 1:1 mixture of diethyl ether and ethyl acetate. Since it was intended to use this penicillin for the preparation of the penicillin of Example XVIII, the isolation procedure was not aimed at the isolation of the product in a substantially pure state but instead directed at the isolation of as much as possible of the desired product. Therefore, the solution was mixed with 70 ml of iced water buffered to pH 7. The well stirred mixture was acidified to pH 5.8 and transferred to a separatory funnel. The water-layer was removed and discarded since it contained the by product N,N'-di-penicillanic acid urea and merely traces of the desired product. The organic layer was then washed twice with slightly acidic ice-cold water and once with a small amount of neutral water. The organic layer, in this way completely freed from the urea and the catalyst, was dried over anhydrous magnesium sulfate, filtered and completely evaporated in the cold.

The residue was dried in vacuo to constant weight to obtain 3.4 g of a slightly yellow, predominantly crystal-

| N—H | about 8.9 (about 0.8 proton) |
| isoxazolyl C$_4$—H | 6.26 (1 proton) |
| C$_5$—H and C$_6$—H | 5.35 →5.60 (multiplet, 2 protons) |
| C$_2$—H | 4.26 (1 proton) |
| α—CH$_2$ | 3.79 (broadened singlet, 2 protons) |
| adamantyl group | 1.90 and 1.73 (centers of somewhat broadened absorptions) } roughly about 22 protons |
| C$_3$—(CH$_3$)$_2$ | 1.64 and 1.51 | line solid 6-{α-p-nitro-benzyloxycarbonylamino-[3-(2,6-dichloro)phenyl-isoxazol-5-yl]-acetamido}penicillanic acid. Thin-layer chromatograms of the final crude product indicated the presence of only the desired penicillin and the starting protected amino acid in about 2:1 ratio. This was confirmed by the PMR spectrum which also revealed the presence of ethyl acetate and a slight amount of water. The calculated amount of the desired penicillin in the crude product was 2.2 to 2.4 g.

EXAMPLE XVIII

6-{α-amino-[3-(2,6-dichloro)phenyl-isoxazol-5-yl]acetamido} penicillanic acid.

tion in water was acidified to pH 4.7 and was extracted twice with an excess volume of ethyl acetate. The water layer was discarded and the combined ethyl acetate layers were washed twice with a small amount of iced water. Thin-layer chromatograms of the final extract showed one elongated (the compound is a D,L-mixture) sulphur and ninhydrin positive spot. After complete evaporation of the extract, a slightly colored solid of 650 mg of dry material was obtained. The final product was examined by IR and PMR spectra and was found to be a 1:1 molar mixture of the desired 6-{α-amino-[3-(2,6-dichloro)phenyl-isoxazol-5-yl]acetamido} penicillanic acid and ethyl acetate possibly contaminated by slight amounts of a 3-(2,6-

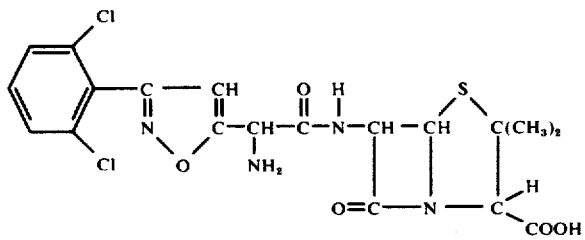

3.0 g of the crude product of Example XVII containing about 2 g of 6-{α-(p-nitro)benzyloxycarbonylamino-[3-(2,6-dichloro)phenyl-isoxazol-5-yl]acetamido}penicillanic acid dissolved in 100 ml of ethylacetate were mixed with 25 ml of water. The pH of the mixture was brought to 7.0 by addition of dilute sodium hydroxide and after the introduction of 1.5 g of Pd/C 10%, hydrogen was continuously passed in beneath the surface. Thin-layer chromatography showed that the reduction was complete after 135 min stirring at room temperature. For 10 minutes, nitrogen was passed through the reaction mixture, ice water added and the pH brought to pH 4.7. The contents of the funnel were transferred to a separatory funnel and the mixture settled to a clear ethyl acetate layer and a water layer separated by an emulsion layer. The water layer was removed and kept aside. Then, the emulsion layer was centrifuged and the resulting layers were separated. The ethyl acetate layer was combined with the first ethyl acetate extract and the water layers were also combined and extracted once with ethyl acetate. The water layer was discarded and remaining catalyst was removed from the collected ethyl acetate extracts by filtration. The colored filtrate was concentrated in vacuo at 0° C to a volume of about 25 ml and 100 ml of iced water were added and the mixture was brought to pH 7.0. The layers were separated and the colored organic layer was discarded. carded. The solution of the desired compound in water was purified by two extractions with a 1:1 mixture of ethyl acetate and diethyl ether. The resulting, practically colorless soludichloro)phenyl-isoxazole-derivative.
Partial analysis of the IR spectrum of the final product (KBr disc, values in cm$^{-1}$):

| | |
|---|---|
| about 3300 | NH |
| about 2600 | OH carboxyl |
| 1780 | C=O β-lactam |
| ± 1730 | C=O ethylacetate |
| ± 1705 | C=O carboxyl |
| 1690 | C=O amide |
| 1390 and 1440 | isoxazole ring absorptions |
| 785 | C—Cl |

EXAMPLE XIX

Sodium salt of
6-{[3-p-nitrophenyl-isoxazol-5-yl]acetamido}penicillanic acid

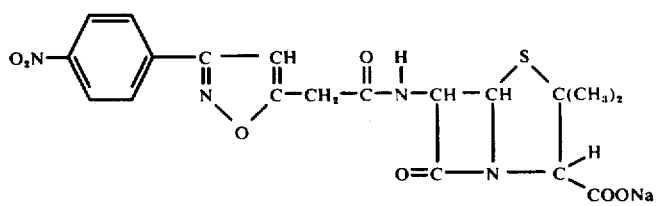

In the usual manner, a reaction was effected with 166 mg (0.67 mmol) of 3-p-nitrophenyl-isoxazol-5-yl-acetic acid, 210 mg (0.67 mmol) of trimethylsilyl-6-isocyanato-penicillanate and a trace of N-isopropyl-benzimidazole, with a solvent of 5 ml of benzonitrile. The reaction was complete after 5 hours stirring at room temperature and the contents of the flask were poured into a ice-cold well stirred mixture of 25 ml of water, 20 ml of diethyl ether and 25 ml of ethyl acetate. The acid mixture (pH3) was neutralized to pH 7 by addition of dilute NaOH, and the layers were separated. The organic layer was discarded and the water layer for purification was extracted once with 40 ml of a 1:1 mixture of ether and ethyl acetate. 30 ml of a 1:1 mixture of ether and ethyl acetate were mixed with the water layer and the pH was lowered to 3.5. The layers were separated and the water layer was again extracted with 50 ml of the same solvent mixture. The combined organic layers were washed twice with a small volume of iced water, then dried over anhydrous magnesium sulfate, filtered and completely evaporated in vacuo. The resulting yellowish oil was triturated with dry diethyl ether. The resulting partly crystalline solid was recovered by filtration and then repeatedly stirred up in ether. After drying in vacuo, the final, colorless product weighed 73 mg. Inspection of the product by thin-layer chromatography and by PMR spectra indicated that the desired 6{[3-p-nitrophenyl-ioxazol-5-yl]acetamido} penicillanic acid contained 5 to 6 moles of water per mole of compound and a small amount of diethyl ether, but that it was virtually pure in other respects. The collected ethereal filtrate and washings were completely evaporated and the residue was dissolved in 3 ml of a dry 1:1 mixture of ether and ethyl acetate and then treated in the cold with a dilute solution of sodium α-ethyl-capronate in ether. The precipitated sodium salt of the said penicillin was recovered by filtration and was repeatedly washed with dry ether. After drying, this product weighed 134 mg. The product was examined in the usual manner. Not counting adhering water (much less than in the case of the free penicillanic acid) the purity of the sodium salt was estimated to be about 80–85% since it contained about 5% by weight of a degradation product and 10–15% by weight of sodium α-ethylcapronate. Analysis of the PMR spectrum of 6-{[3-p-nitrophenyl-isoxazol-5-yl]acetamido} penicillanic acid dissolved in a mixture of about 6 parts of hexadeuterodimethylsulphoxide and 1 part of $D_2O$ (60 Mc, δ-values in ppm, internal reference 2.2-dimethylsilapentane-5-sulphonate):

| $C_6H_4$ | 7.95 →8.4 (AA'BB' splitting pattern, 4 protons) |
|---|---|
| isoxazolyl | |
| $C_4-H$ | 6.94 (1 proton) |
| $C_5-H$ and $C_6-H$ | 5.5 (slightly broadened singlet, 2 protons) |
| $C_2-H$ | 4.15 (1 proton) |
| α—$CH_2$ | 4.0 (somewhat broadened singlet, 2 protons) |
| $C_3-(CH_3)_2$ | 1.63 and 1.52 (6 protons) |

Partial analysis of the IR of the sodium salt of 6- [3-(4-nitro)phenyl-isoxazol-5-yl]acetamido penicillanic acid (KBr disc, values in $cm^{-1}$):

| about 3380 | NH |
|---|---|
| 1770 | C=O β-lactam (intensive) |
| 1675 | C=O amide (intensive) |
| 1600 | C=O carboxylate ion + probably C=C aromatic (very intensive) |
| 1525 | $NO_2$ + possibly NH def. (very intensive) |
| 1400 – 1460 | isoxazole ring absorptions |
| 1355 | $NO_2$ (intensive) |
| ± 858 | C—$NO_2$ and aromatic substitution pattern |

(medium intensities)

EXAMPLE XX

6-{α-carbamyl-[3-(2,6-dichloro)phenyl-isoxazol-5-yl]acetamido} penicillanic acid

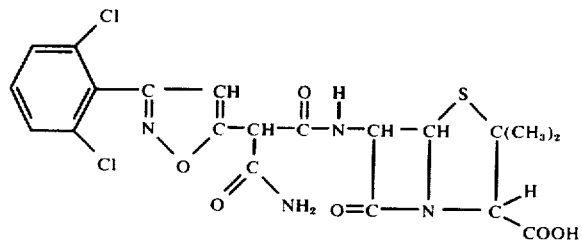

A solution of 3.7 mmol of n-butyllithium in hexane was added drop-wise to a solution of 1.0 g (3.7 mmol) of 3-(2,6-dichloro)phenyl-isoxazol-5-yl-acetamide in 15 ml of dry tetrahydrofuran cooled down to −70° C. The rate of addition was adjusted to reaction temperatures below −60° C. After a few minutes additional stirring at −70° C, 0.47 ml (approximately 3.7 mmol) of freshly distilled trimethylchlorosilane were introduced drop-wise. Afterwards the cooling bath was removed and the temperature was allowed to rise to −30° C. This procedure — addition successively of 1 equivalent of n-butyllithium and 1 equivalent of trimethylchlorosilane — was repeated in the same fashion. To the now in situ prepared solution of N,N-bis-trimethylsilyl derivative of the starting product in a mixture of 15 ml of tetrahydrofuran and about 3.5 ml of hexane 0.56 ml (3.7 mmol) of N,N,N',N'-tetramethylethylene-diamine was added. The mixture was again cooled down to −75° C and a solution of about 3.7 mmol of n-butyllithium in 1.76 ml of hexane was added drop-wise. The rate of addition was adjusted to reaction temperatures of maximum −70° C. The reaction mixture was additionally stirred for one hour at −70° to −60° C. The sequence of reaction was completed by the dropwise addition of a solution of 1.16 g (3.7 mmol) of trimethylsilyl 6-isocyanato-penicillanate in 10 ml of dry toluene whereby the reaction temperature was not allowed to rise above −55° C. The reaction mixture was then stirred at −60° C for 30 min. and the reaction mixture and dilute hydrochloric acid were slowly and simultaneously poured into a well stirred and icy-cold mixture of 50 ml of diethyl ether and 50 ml of water of pH 4. Then the pH of the mixture was raised to 7 and the layers were separated. The water layer was again extracted with 50 ml of ether at pH 7 and the organic layers were discarded. The water layer was extracted three times with ether successively at pH 5.0, 4.5 and 4.3 and once extracted with a 1:1 mixture of ethyl acetate and diethyl ether at pH 4.3 Thin-layer chromatography showed that the water layer no longer contained the desired penicillin accompanied with small amounts of sulphur containing impurities and that the first three ethereal extracts contained 6-{α-carbamyl-[3-(2,6-dichloro) phenyl-isoxazol-5-yl]acetamido}penicillanic acid in a substantially pure state. The ethereal extracts were combined, washed with iced water, dried over anhydrous magnesium sulfate, filtered and completely evaporated in vacuo. The obtained solid weighed 500 mg after prolonged drying in vacuo. IR and PMR spectra of the final product confirmed the alleged structure of the penicillin. The estimated purity was 80–85%. Partial analysis of the IR spectrum of the final product (KBr disc, values in cm$^{-1}$);

| | |
|---|---|
| ± 3440 | NH (presumably of CO—NH$_2$) |
| ± 3330 | NH (presumably of CO—NH) |
| ± 3210 | NH (presumably bonded NH) |
| 2500–2650 | OH (carboxyl) |
| 1780 | C=O β-lactam |
| ± 1720 | C=O (carboxyl) |
| 1690 and 1660 | C=O of CO—NH and CO—NH$_2$ |
| 1598 | C=C aromatic and NH$_2$ deformation |
| ± 1525 | presumably NH deformation |
| 1395, 1430 | isoxazole ring absorptions |
| 790 | C—Cl and aromatic substitution pattern. |

EXAMPLE XXI

6-{[3-methyl-isoxazol-5-yl]acetamido}penicillanic acid

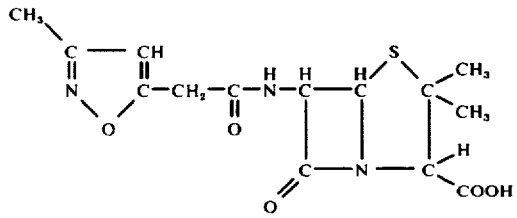

Using the procedure of Example II 282 mg (2 mmol) of 3-methyl-isoxazol-5-yl acetic acid were reacted with 628 mg (2 mmol) of trimethylsilyl 6-isocyanato-penicillanate in 10 ml of dry dichloromethane in the presence of three drops of N-isopropyl benzimidazole (a catalyst). After the usual working up of the reaction mixture a slightly coloured product was obtained of good purity according to TLC, IR- and PMR-spectra. Analysis of the PMR spectrum of the product, 6- [3-methyl-isoxazol-5-yl]acetamido penicillanic acid, dissolved in hexadeutero DMSO with some D$_2$O added (60 Mc, δ-values in ppm, tetramethylsilane as an internal standard):

| | |
|---|---|
| isoxazolyl C$_4$—H | 6.22 |
| C$_5$—H and C$_8$—H | 5.50 (2 protons) |
| C$_2$—H | 4.32 |
| CH$_2$—CO— | 3.82 (2 protons) |
| isoxazolyl—CH$_3$ | 2.23 |
| C$_3$—(CH$_3$)$_2$ | 1.65 and 1.52 |

Partial analysis of the IR-spectrum of the final product (in KBr, values in cm$^{-1}$):

| | |
|---|---|
| ± 3500 | OH carboxyl |
| 3350 | NH |
| 1780 | C=O β-lactam |
| 1740 | C=O carboxyl |
| 1670 | C=O amide |
| 1380–1430 | isoxazole ring absorptions |

EXAMPLE XXII

7-{[3-methyl-isoxazol-5-yl]acetamido}cephalosporanic acid

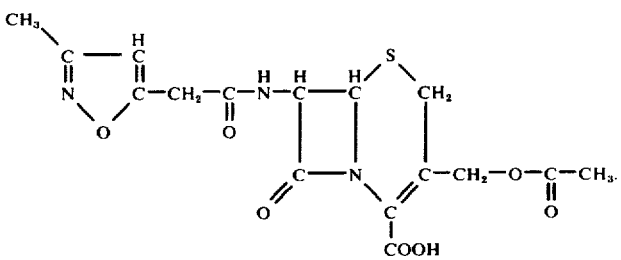

Using the procedure of Example III 3-methyl-isoxazol-5-yl a-cetylchloride (prepared from 4.5 mmoles of 3-methyl-isoxazol-5-yl acetic acid and thionyl chloride) was brought into reaction with N,O-bis-trimethylsilyl 7-amino cephalosporanate (prepared from 1.224 mg (4.5 mmoles) of 7-ACA. After the reaction and working up of the reaction mixture 790 mg (44 %) of a slightly yellow coloured product, 7-{[3-methyl-isoxazol-5-yl]acetamido } cephalosporanic acid was isolated with a purity about 70% according to TLC, IR- and PMR-spectra.

Analysis of the PMR-spectra of the final product dissolved in a mixture of deuterochloroform and hexadeutero DMSO with some D$_2$O added (60 Mc, δ-values in ppm, tetramethylsilane as an internal standard):

| | |
|---|---|
| isoxazolyl C$_4$—H | 6.12 |
| C$_7$—H | 5.75 and 5.66 (J≈4.5 cps, 1 proton) |
| C$_6$—H | 5.05 and 4.97 (J≈4.5 cps, 1 proton) |
| CH$_2$—CO— | 3.78 (2 protons) |
| O—CH$_2$— | 5.22 →4.68 (J≈13 cps, 2 protons) |
| S—CH$_2$ | 3.80 →3.15 (J≈18 cps, 2 protons) |
| CO—CH$_3$ | 2.07 |
| isoxazolyl—CH$_3$ | 2.25 |

Partial analysis of the IR-spectrum of the final product (KBr, values in cm$^{-1}$):

| | |
|---|---|
| ± 3280 | OH |
| 1780 | C=O β-lactam |
| 1750 | C=O ester |
| 1670 | C=O amide |
| 1230 | C—O—C ester |

| | |
|---|---|
| 1380 and 1420 | isoxazole ring absorptions |

EXAMPLE XXIII

Sodium salt of 6-{α-(N-phenyl)carbamyl-[3-(2.6-dichloro)phenyl-isoxazol-5-yl]acetamido}penicillanic acid

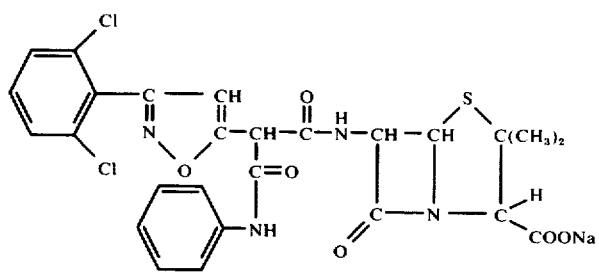

A solution of 1.0 g (2.9 mmol) of N-phenyl-3-(2.6-dichloro) phenyl-isoxazol-5-yl-acetamido in 15 ml of dry tetrahydrofurane was cooled down to −70° C. At −70° C were in succession dropwise introduced a precooled solution of about 2.9 mmol of n-butyllithium in 5 ml of a mixture of n-hexane and dry tetrahydrofurane, next 0.44 ml (about 2.9 mmol) of N,N,N',N'-tetramethylethylene-diamine and finally again a precooled solution of 2.9 mmol of n-butyllithium in 5 ml of a mixture of n-hexane and dry tetrahydrofurane. The reaction mixture was additionally stirred during 1 hour at −70° C. To the in this manner prepared reagent was subsequently added dropwise (at −70° C) a solution of 0.91 g (2.9 mmol) of trimethylsilyl 6-isocyanatopenicillanate in 5 ml of dry toluene. After completion of the addition the temperature of the reaction mixture was allowed to rise to −50° C, at which temperature stirring was continued during approximately 30 minutes. Then, the reaction mixture and diluted hydrochloric acid were added simultaneously to a well stirred mixture of 30 ml of water and 30 ml of diethylether cooled down to 0° C. The rates of addition were mutually balanced to give a pH of approximately 7.5 throughout the neutralisation. The resulting layers were separated and the water-layer for purification once extracted with 30 ml of diethyl ether and once with 30 ml of ethyl acetate. The combined organic layers and the water-layer were inspected by thin-layer chromatography (detection of sulphur containing compounds) with as eluent a 98:2 mixture of diethylether and formic acid. The combined organic layer did not contain such compounds and was discarded. The chromatogram of the water-layer showed 4 well-separated spots, three minor ones and one major spot. The minor spots were attributed respectively to degradation product(s), to N,N'-dipenicillanylurea and to n-butyl-carbonamido-penicillanic acid. The Rf-values of the latter two spots were found to be equal to the Rf-values of the actual penicillins. In order to separate the compound responsible for the fourth and major spot on the chromatogram, the water-layer was extracted at pH 4.9 and pH 3.6 with 30 ml of diethyl ether, which resulted in complete removal of the desired compound from the water-layer. The remainder and part of the third compound (presumably n-butylpenicillin) were removed by extraction at pH 3.3 with a 2:1 mixture of diethyl ether and ethylacetate. In order to remove the byproduct, this layer was repeatedly washed with iced water of pH 4.6, which resulted in another (the third) almost clean extract and a number of washings still containing considerable amounts of the desired product. The fourth extract was obtained by extraction of the combined washings at pH 6.0 with ethyl acetate. The four extracts were combined, washed with iced water, dried on anhydrous magnesium sulfate, filtered and concentrated in vacuo. The concentrated solution of the desired compound in ethyl acetate was treated with a concentrated solution of sodium α-ethyl capronate in ethyl acetate. The sodium salt of the penicillin was precipitated from this addition of dry diethyl ether. The precipitate was collected by filtration, washed with diethyl ether and dried to constant weight, to obtain 580 mg of the sodium salt of 6-{α-(N-phenyl)carbamyl-[3-(2.6-dichloro)phenyl-isoxazol-5-yl] acetamido}penicillanic acid. The final product was inspected by thin-layer chromatography, IR spectra and PMR spectra, which confirmed the alleged structure and indicated the impurities of the final product: some sodium α-ethyl capronate and a slight amount of degradation product(s). Partial analysis of the IR spectra of the final product and of the starting product (solutions in chloroform, conc. about 10 mg/ml, values in cm$^{-1}$):

| | Final Product | N-phenyl-3-(2.6-dichloro) phenyl-isoxazol-5-yl-acetamido |
|---|---|---|
| ±3420 | NH (presumably of $C_6H_5$—NH—CO—) | 3430 NH |
| ±3300 | NH (broad) | |
| 1775 | C=O β-lactam (intensive) | |
| ±1705 | C=O amide (very intensive) | 1695 C=O amide (intensive) |
| 1600 | C=O carboxylate ion and C=O arom. (very intensive) | 1598 C=C arom. (intensive) |
| 1558 | C=C and/or C=N (sharp, medium intensity) | 1557 C=C and/or C=N (sharp, medium intensity) |
| 1500–1550 | presumably NH deformation | ±1520 presumably NH deformation (medium intensity) |
| 1495 | C=C arom. (medium in- | 1496 C=C arom. (medium in- |

| tens.) | | tens.) | |
|---|---|---|---|
| ±1440 | med. intens. ⎫ isoxazolering | 1435 intensive ⎫ isoxazolering | |
| 1380 | med. intens. ⎭ absorptions | 1380 med. intens. ⎭ absorptions | |
| 783 (in KBr disc) C—Cl (intens.) | | 785 (in KBr disc) ⎫ C—Cl medium | |
| | | 772 (in KBr disc) ⎭ intensities | |
| 752 (in KBr disc) possibly aromatic subst. pat. (med. intensity) | | 755 (in KBr disc) possibly aromatic subst. pat. (med. intensity) | |

EXAMPLE XXIV

7-{[3-(4-nitro)phenyl-isoxazol-5-yl]acetamido}cephalosporanic acid

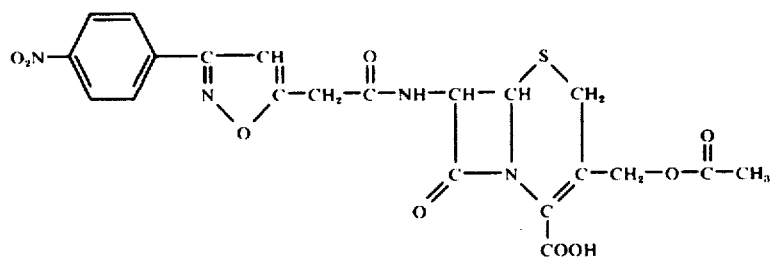

Using the procedure of Example III 3-(4-nitro)phenyl-isoxazol-5-yl acetyl chloride (prepared from 1.64 g (6.6 mmol) of the corresponding acetic acid and thionyl chloride) was brought into reaction with N,O-bis-trimethyl-silyl-7-amino-cephalosporanate (in situ prepared from 1.8 g (6.6 mmoles) of 7-ACA). The reaction was worked up in the usual fashion. 1350 mg (40%) of a slightly yellow coloured solid was isolated. According to thin-layer chromatography, IR and PMR spectra, the purity of the final product, 7-{[3-(4-nitro)-phenyl-isoxazol-5-yl]acetamido} cephalosporanic acid, was about 85%. Analysis of the PMR spectrum of the final product dissolved in hexadeuterodimethylsulphoxide (60 Mc, δ-values in ppm, internal reference 2.2-dimethylsilapentane-5-sulphonate):

| N—H | 9.36 and 9.22 (J=8.0 ± 0.5 cps, about 0.8 proton) |
|---|---|
| $C_6H_4$ | 7.9 ⟶ 8.5 (AA'BB' splitting pattern, 4 protons) |
| isoxazolyl $C_4$-H | 7.05 (1 proton) |
| $C_7$—H | 5.87, 5.79, 5.73 and 5.65 (slightly broadened signals, J=8.0 cps and $J_{AB}$≈4.6 cps, 1 proton) |
| $C_6$—H | 5.19 and 5.11 ($J_{AB}$ = 4.6 ± 0.2 cps) ⎫ 3 protons |
| O—CH₂ | (5.19), 4.97, 4.82 and 4.60 ($J_{AB}$ = 13.0 ± 0.2 cps) |
| CH₂—CO | about 4.0 (slightly broadened singlet, 2 protons) |
| S—CH₂ | about 3.6 (center of AB-quartet with very weak outer lines, 2 protons) |
| CO—CH₃ | 2.06 (3 protons) |

EXAMPLE XXV

The compounds of examples I to XX were tested for antibiotic activity in vitro with an agar serial dilution test which was carried out as follows: A stock of the antibiotic at 2,000 g/ml was prepared in a sterile suitable vehicle and two-fold dilutions were made with sterile 1/20 Mol phosphate buffer pH 6.5 ($KH_2PO_4$—NaOH). 1 ml quantities of each dilution were incorporated in 19 ml brain-heart infusion agar in sterile Petri dishes and the hardened surface was inoculated with test organisms and incubated 24 hours at 37° C. The minimal inhibitory concentration (MIC) was expressed in μg/ml: the least amount of antibiotic that completely inhibited the test organism. The MIC values of the product, and of Cloxacillin, Nafcillin, Dicloxacillin, Cephalexin, Cephalotin and Cephaloridin, as references, are shown in the following tables:

| | MIC's in μg/ml | | | | | | | | | |
|---|---|---|---|---|---|---|---|---|---|---|
| Test organism | Example I | Example II | Example III | Example IV | Example V | Example VI | Example VII | Example VIII | Example IX | Example X |
| Gram pos. | | | | | | | | | | |
| Bacillus subtilis ATCC 6633 | 0.007 | 0.007 | ±0.007 | 1 | 0.5 | 0.03 | 0.015 | 0.25 | 0.12 | 0.005 |
| Staphylococcus aureus A55 | 0.01 | 0.01 | 0.015 | 0.75 | 1 | 0.06 | 0.06 | 1.5 | 0.25 | 0.03 |
| A321 | 0.015 | 0.015 | ±0.007 | 0.5 | 1 | 0.06 | 0.06 | 0.5 | 0.25 | 0.03 |
| A355') | 3 | 3 | 0.12 | 3 | 12.5 | 3 | 0.25 | 3 | 25 | 3 |
| L160a') | 1 | 1 | 0.06 | 1.5 | 3 | 0.5 | 0.12 | 3 | 25 | 0.5 |
| Streptococcus haemolyticus A266 | 0.007 | 0.007 | ±0.007 | 0.5 | 0.5 | 0.012 | 0.03 | 0.25 | 0.06 | 0.006 |
| Streptococcus faecalis L 80 | 50 | 50 | 0.5 | 12.5 | 25 | 0.25 | 1 | 100 | 1.5 | 0.25 |
| Diplococcus pneumoniae L 54 | 0.25 | 0.25 | ±0.007 | 0.75 | 6 | 0.03 | 0.03 | 1 | 0.12 | 0.02 |
| Gram neg. | | | | | | | | | | |
| Brucella melitensis A488 | 0.5 | 0.5 | 1 | 12.5 | 25 | 3 | 12.5 | 12.5 | 25 | 3 |

-continued

| | MIC's in µg/ml | | | | | | | | | |
|---|---|---|---|---|---|---|---|---|---|---|
| Test organism | Example I | Example II | Example III | Example IV | Example V | Example VI | Example VII | Example VIII | Example IX | Example X |
| Pasteurella multocida A723 | 2 | 2 | 1 | 6 | 1.5 | 12.5 | 50 | 100 | 25 | 3 |
| Klebsiella pneumoniae A809 | 100 | 100 | 12.5 | >100 | >100 | 100 | 50 | >100 | >100 | >100 |

')Penicillinase-producing

| | MIC's in µg/ml | | | | | | |
|---|---|---|---|---|---|---|---|
| Test organism | Example XI | Example XII | Example XIII | Example XIV | Example XV | Example XVI | Example XVII |
| Gram pos. | | | | | | | |
| Bacillus subtilis ATCC 6633 | 0.06 | 0.06 | 1 | 3 | 0.25 | 0.03 | 0.5 |
| Staphylococcus aureus A55 | 0.12 | 0.25 | 3 | 12.5 | 0.5 | 0.5 | 1 |
| A321 | 0.06 | 0.12 | 1.5 | 12.5 | 1 | 0.03 | 1 |
| A355') | 12.5 | 0.25 | 6 | >100 | 12.5 | 12.5 | 12.5 |
| L160a') | 12.5 | 0.25 | 6 | >100 | 12.5 | 12.5 | 6 |
| Streptococcus haemolyticus A266 | 0.007 | 0.06 | 0.6 | 1.5 | 0.06 | <0.015 | 0.06 |
| Streptococcus faecalis L 80 | 1.5 | 6 | 100 | 50 | 0.5 | 0.25 | 3 |
| Diplococcus pneumoniae L 54 | 0.12 | 0.06 | 1.5 | 6 | 0.03 | 0.06 | 0.5 |
| Gram neg. | | | | | | | |
| Brucella melitensis A488 | 3 | 50 | >100 | 50 | 6 | 3 | 25 |
| Pasteurella multocida A723 | 50 | 100 | >100 | 50 | 12.5 | 6 | 50 |
| Klebsiella pneumoniae A809 | 100 | >100 | >100 | >100 | >100 | >100 | >100 |

| | MIC's in µg/ml | | | | | | | | |
|---|---|---|---|---|---|---|---|---|---|
| Test organism | Example XVIII | Example XIX | Example XX | Cloxazilline | Nafcilline | Dicloxacilline | Cephalexine | Cephalotine | Cephaloridine |
| Gram pos. | | | | | | | | | |
| Bacillus subtilis ATCC 6633 | 0.06 | <0.015 | 0.25 | 0.25 | 0.5 | 0.12 | 0.5 | 0.03 | 0.06 |
| Staphylococcus A55 | 0.25 | 0.03 | 0.25 | 0.12 | 0.12 | 0.06 | 3 | 0.25 | 0.06 |
| A321 | 0.12 | 0.03 | 0.25 | 0.06 | 0.25 | 0.12 | 1.5 | 0.25 | 0.06 |
| A355') | 12.5 | 1 | 3 | 0.5 | 1 | 0.5 | 12.5 | 1 | 0.12 |
| L160*') | 12.5 | 3 | 3 | 1 | 0.5 | 0.25 | 12.5 | 1 | 0.06 |
| Streptococcus haemolyticus A266 | <0.015 | 1.5 | 0.03 | 0.25 | 0.015 | 0.06 | 0.25 | 0.06 | 0.015 |
| Streptococcus faecalis L 80 | 1 | 1 | 0.5 | 25 | 10 | 12.5 | 100 | 25 | 12.5 |
| Diplococcus pneumoniae L 54 | 0.12 | 0.03 | 0.06 | 1.5 | 0.06 | 0.5 | 3 | 0.25 | 0.015 |
| Gram neg. | | | | | | | | | |
| Brucella melitensis A488 | 0.5 | 0.12 | 3 | 100 | 6 | >100 | 6 | 6 | 3 |
| Pasteurella multocida A723 | 6 | 1 | 6 | 6 | 12.5 | 6 | 3 | 0.25 | 1 |
| Klebsiella pneumoniae A809 | >100 | 100 | >100 | 6 | 12.5 | 25 | 3 | 0.5 | 3 |

| | MIC's in µg/ml | | | |
|---|---|---|---|---|
| Test organism | EXAMPLE XXI | EXAMPLE XXII | EXAMPLE XXXIV | EXAMPLE XXXV |
| Gram pos. | | | | |
| Bacillus subtilis ATCC 6633 | 0.06 | 0.06 | 0.75 | 0.06 |
| Staphylococcus aureus A 55 | 0.5 | 0.5 | — | 0.25 |
| A 321 | 0.25 | 0.5 | 1.5 | 0.25 |
| A 355 ') | 6. | 1 | 1.5 | 0.5 |
| L 160 a') | 3. | 1 | — | 0.5 |
| Streptococcus haemolyticus A 266 | 0.03 | 0.12 | — | 0.06 |
| Streptococcus faecalis L 80 | 3 | 25 | 12.5 | 25 |
| Diplococcus pneumoniae L 54 | 1.5 | 0.5 | 0.25 | 1 |
| Gram neg. | | | | |
| Brucella melitensis A 488 | 3 | 12.5 | — | 0.06 |
| Pasteurella multocida A 723 | 1.5 | 3 | 3 | 0.75 |
| Klebsiella pneumoniae A 809 | >100 | 3 | 12.5 | 1.5 |
| Brucella Suis A 2126 | — | — | 1.5 | — |

EXAMPLE XXVI

A. The compounds prepared in examples I, II, III, IV, V, VII, IX and XI were tested in vivo together with some reference compounds.
Tested animals: female mice (Swiss), weight 20 g.
Infection way: intraperitoneal
Therapeutics: the tested compound dissolved in a physiological NaCl-solution, 3 × ⅓ dose after every two hours. The first dose was administered just after the infecton.
$ED_{50}$ - calculation: according to Horn (1956)
The results are summarized in the following table.

| | Example I/II | | | Example V | | | Example III | | | Example IV | | | Example VII | | |
|---|---|---|---|---|---|---|---|---|---|---|---|---|---|---|---|
| | ED₅₀ mg/kg in experiments with mice. | | | | | | | | | | | | | | |
| Inf. | i.p. | | | i.p. | | | i.p. | | | i.p. | | | i.p. | | |
| Ther. | i.p. | s.c. | p.o. | i.p. | s.c. | p.o. | i.p. | s.c. | p.o. | i.p. | s.c. | p.o. | i.p. | s.c. | p.o. |
| A | 10,8 | 36,9 | 126,0 | <100 | | >215 | <0,465 | 5,11 | 61,9 | 23,3 | 31,6 | 50,1 | 3,8 | 18,5 | 70,0 |
| B | >215 | >215 | >215 | | | | 2,87 | >215 | ±200 | 23,3 | >215 | ±200 | 17,1 | 140,0 | >215 |
| C | 133,0 | >215 | >215 | | | | 1,78 | 75,0 | >215 | 19,6 | >215 | >215 | | | |
| D | >215 | | | | | | ±200 | | | >215 | | | >215 | | >215 |
| E | >215 | | | | | | >215 | | | >215 | | | >215 | | >215 |
| F | | | | | | >300 | ±200 | | >300 | >215 | | | >215 | | ±215 |

| | Example IX | | | Example XI | | | Propicillin | | | Dicloxacillin | | | Keflin (Cefalotin) | | |
|---|---|---|---|---|---|---|---|---|---|---|---|---|---|---|---|
| Inf. | i.p. | | | i.p. | | | i.p. | | | i.p. | | | i.p. | | |
| Ther. | i.p. | s.c. | p.o. | i.p. | s.c. | p.o. | i.p. | s.c. | p.o. | i.p. | s.c. | p.o. | i.p. | s.c. | p.o. |
| A | >21,5 | | >100 | >21,5 | | >100 | 0,926 | 2,33 | 10,8 | 0,909 | 126 | 92,6 | 1,90 | 16,2 | 14.7 |
| B | | | | | | | 133 | >215 | >215 | 1,71 | 133 | 110 | 27,1 | >215 | 68,1 |
| C | | | | | | | 88 | >215 | >215 | 5,84 | 92,6 | 92,6 | 20 | 110 | 147 |
| D | | | | | | | | | | | | | 79,4 | ±200 | |
| E | | | | | | >300 | | | | | | | >215 | >215 | |
| F | | | | | >300 | >300 | | | | | | | 79,4 | 68,1 | |

A = *Staphylococcus aureus* A 321
B = *Staphylococcus aureus* A 2001
C = *Staphylococcus aureus* A 2000
D = *Salmonella typhi murium* R 172
E = *Pseudomonas aeruginosa* A 1058
F = *Proteus mirabilis* O.T.

B. Activity of the compound of example III in a prophylactic experiment against an infection with Staphylococcus aureus A 321.

Tested animals: female mice (Swiss), weight 20 g.
Administered doses: Tested compound dissolved in physiological NaCl-solution.
Group A: one dose administered four hours before the intraperitoneal infection
Group B: one dose administered two hours before the intraperitoneal infection.

| mice-group | infection way | administration | ED₅₀ in mg/kg Tested compound | Dicloxa-cillin |
|---|---|---|---|---|
| A | i.p. | i.p. | 21.5–46.5 | <21.5 |
| | i.p. | per os | ±465 | 46.5–100 |
| B | i.p. | i.p. | <21.5 | 46.5–100 |
| | i.p. | per os | <21.5 | 215–465 |

C. Serum levels of the tested compound and dicloxacillin. The serum levels of dicloxacillin and the compound of example III were determined after an intramuscular administration of 50 mg/kg of these compounds in an aqueous solution in rabbits. The serum levels are reported in the following table.

| Test compound | Hours after injection | Serum level in γ/ml |
|---|---|---|
| Dicloxacillin | 1 | 27 |
| | 2 | 18.8 |
| | 4 | 7.1 |
| Example III | 1 | 5.4 |
| | 4 | 2.2 |

Peak blood levels of the two drugs were reached after 1 hour with the tested compound giving levels of 5.4 μg/ml and dicloxacillin 27 μg/ml. After 4 hours, these levels were 2.2 μg/ml and 7.1 μg/ml respectively. Dicloxacillin was almost completely bound to serum protein whereas the tested compound appeared to be bound to the extent of about 50%. Thus, the amount of free drug in the serum was of the same order. However, the M.I.C. values for the tested compound were approximately 5 – 10 times less so that the overall result was better and this was reflected in the in vivo results.

EXAMPLE XXVII

A quantity of 100 to 2000 mg of the sodium salt of 7-{[3-(2,6-dichlorophenyl)-isoxazol-5-yl]-acetamido}cephalosporanic acid was aseptically introduced into a vial suitable for injectable compositions. Before use, the powder was dissolved in a suitable amount of sterile and pyrogen-free water.

EXAMPLE XXVIII

Syrups were prepared from the compounds obtained according to Examples I-XXIV by mixing the following ingredients:

| | |
|---|---|
| sodium salt of the desired compound | 1.5 – 6 g |
| soluble starch | 1 – 3 g |
| sodium saccharin | 0.1 – 1 g |
| nipa M | 0.06 g |
| strawberry flavor | 0.1 – 5 g |
| amaranth | 0.010 g |
| saccharose | 30 g |
| water added to a volume of | 60 ml |

These prepared syrups were suitable for oral administration.

EXAMPLE XXIX

Capsules were prepared in the usual way containing as active ingredient the compound obtained according to Examples I-XXIV. The components of the capsules are listed below:

| | |
|---|---|
| sodium salt of the desired compound | 150–500 mg |
| potassium bicarbonate | 100–300 mg |
| magnesium stearate | 2–10 mg |
| lactose | q.s. for 1 capsule |

These capsules could be used for oral administration.

EXAMPLE XXX

Tablets were prepared in the usual way containing as active ingredient the compounds of Examples I – XXIV. The components of the tablets are listed below:

| | |
|---|---|
| sodium salt of the desired compound | 125–500 mg |
| polyvinylpyrrolidone | 5–30 mg |
| amylum maidis | 100–300 mg |
| magnesium stearate | 1–20 mg |
| lactose | q.s. for 1 tablet |

These tablets could be used for oral administration.

EXAMPLE XXXI 3-methyl-isoxazol-5-yl acetic acid 1.0 mole of acetylacetone, 1.1 mole of hydroxylamine and 2.0 moles of sodium carbonate were reacted and the temperature rose to 35° C after the carbonate addition. The mixture was stirred for 2½ hours and was extracted with diethyl ether to obtain a 56% yield of 3,4-dimethylisoxazole.

200 ml of 20% of n-butyl lithium in hexane were added under nitrogen atmosphere to a solution of 38.8 g (0.4 mole) of 3,5-dimethyl isoxazole in 350 ml of freshly distilled THF cooled to −75° C while maintaining the temperature below −55° C and after stirring for 30 minutes, the mixture was poured onto solid carbon dioxide. Water and ethyl acetate were added thereto and the resulting aqueous layer was extracted at a pH of 2 with ethyl acetate. The combined organic layers were dried over magnesium sulfate, treated with activated carbon and concentrated under reduced pressure. The 25.7 g of brown colored residue was treated with cold chloroform and a 1–1 chloroform-carbon tetrachloride mixture to obtain 23.0 g (41% yield) of 3-methyl-isoxazole-5-yl acetic acid in the form of a white solid melting at 102°–103° C.

EXAMPLE XXXII 3-methyl-4-chloro-isoxazol-5-yl acetic acid

A mixture of 12 g of 4-chloro-3,5-dimethyl isoxazole (prepared by chlorination of 3,5-dimethyl-isoxazole in acetic acid at 50° C) in freshly distilled THF and 13.8 ml of tetramethylenediamine in a 3-necked vessel was reacted under a nitrogen atmosphere with 50 ml of a 20% n-butyl lithium solution in hexane at −70° C and the mixture was stirred for 2 hours. A stream of carbon dioxide was passed therethrough for an hour and then water and diethyl ether were added thereto. The aqueous layer was extracted with diethyl ether at a pH of 2 and the combined organic layers were dried over magnesium sulfate, treated with activated carbon and concentrated to dryness under reduced pressure. The 6.3 g of product was crystallized from a petroleum ether-acetone mixture to obtain 3-methyl-4-chloro-isoxazole-5-yl acetic acid melting at 128°–131° C (sublimation)

EXAMPLE XXXIII 3-t-butyl-isoxazol-5-yl acetic acid 2.87 ml (20.6 mmol) of triethylamine in 25 ml of diethyl ether were added to a solution of 2.50 g (18.4 mmol) of 2,2-dimethylpropane-hydroxamic acid chloride [Zinner et al, Chem. Ber., Vol. 98 (1965), p.1353] and 3.0 ml of condensed propyne in 50 ml of diethyl ether cooled in an icebath for 2 hours. The reaction mixture in the bath was stirred for another 20 hours and the precipitate formed was filtered off. The filtrate was concentrated in vacuo (20 mm Hg) to obtain 2.38 g of a yellow oily residue which was distilled in vacuo to obtain a colorless oil with a boiling point of 42° C at 11 mm.Hg, which was 3-t-butyl-isoxazol-5-yl acetic acid. 21 ml of a 20% solution of n-butyl lithium in hexane were added over 85 minutes under a nitrogen atmosphere to a solution of 5.76 g (41 mmol) of 3-t-butyl-5-methyl-isoxazole in 70 ml of freshly distilled THF in a 3-necked vessel while keeping the temperature at −65° to −70° C. The mixture was stirred for 1 hour at −65° to −70° C and was then poured over solid carbon dioxide. Water and diethyl ether were added to the mixture and the aqueous phase was extracted at a pH of 2.8 with diethyl ether. The combined ether phases were evaporated to obtain 3.7 g of a yellowish solid which was crystallized from a benzene-n-hexane mixture to obtain 3.0 g of 3-t-butyl-isoxazol-5-yl acetic acid in the form of white crystals melting at 108°–109° C.

EXAMPLE XXXIV sodium 7-[3-(t-butyl)isoxazole-5-ylacetamido]-3-acetoxymethyl 3-cephem-4-carboxylate

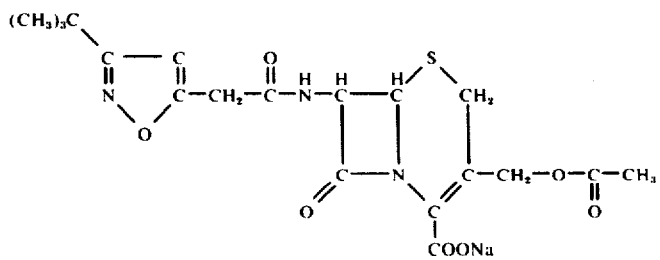

5 mmoles of 3(t-butyl)isoxazole-5 yl acetylchloride were prepared from 3(t-butyl)isoxazole-5-yl-acetic acid and thionylchloride in tetrachloromethane.

After evaporation in vacuo the residue was taken up in 7 ml of dry ethyl acetate. 1.36 g of 7-aminocephalosporanic acid (5 mmoles) were suspended in 30 ml of ethyl acetate under an atmosphere of nitrogen. The suspension was cooled in an ice-bath and 1.4 ml of triethylamine were introduced. After 5 minutes 1.3 ml of trimethylchlorosilane were added to the mixture and stirring was continued for one hour at room temperature.

The mixture was cooled again, and, after addition of 0.59 ml of chinolin, the 3(t-butyl)isoxazole 5-yl-acetylchloride in 15 ml of ethyl acetate was added dropwise to the reaction mixture, causing a rise of the reaction-temperature of 5° C.

After the addition, the icebath was removed and the reactionmixture was stirred half an hour at room temperature.

Then the reactionmixture was poured into a mixture of water and ethylacetate with ice cooling while pH was kept at 7.0.

The aqueous layer was extracted at a pH of 6.5 and subsequently at pH values of 5.0 to 3.0, while each time the pH value was decreased half a unity and using 25 ml of ethyl acetate pro extraction. The extracts were combined, washed with iced water (2 × 10 ml) and dried on anhydrous magnesium sulfate. After treatment with activated coal the solvent was evaporated in vacuo and 1.24 g of an amorphous product were obtained, identified as 7[3-t-butyl) isoxazole-5 yl-acetamido] 3-acetoxymethyl-3-cephem-carboxylic acid.

0.88 g of this obtained acid were dissolved in 10 ml of dry ethyl acetate. After addition of the calculated amount of sodium α-ethylhexanoate no precipitate was formed. The solution was concentrated and diluted with diethyl ether. The formed precipitate was filtrated and dried after intensive washing with diethyl ether. Yield: 0.57 g of sodium 7[3-(t-butyl) isoxazole-5 yl-acetamido]-3-acetoxymethyl-3-cephem-carboxylate, the alleged structure of which was confirmed by IR and PMR spectra.

EXAMPLE XXXV

Sodium 7{[3-methyl-4-chloroisoxazole-5 yl] acetamido}-3-acetoxymethyl-3-cephem-4carboxylate

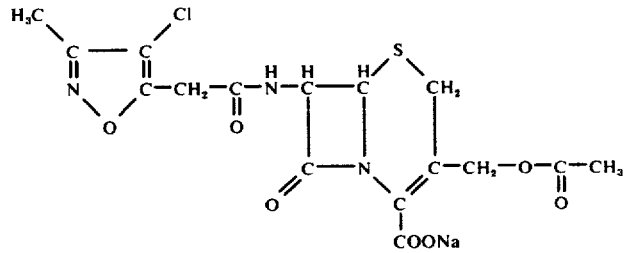

702 mg. (4 mmol) of 3-methyl-4-chloroisoxazole-5-yl- acetic acid, 10 ml of tetrachloromethane, 0.42 ml of thionylchloride and two drops of dimethylformamide were refluxed during one hour, whereafter the acid was converted in the corresponding acid chloride and the solvents were removed by distillation.

The obtained acid chloride, dissolved in 6 ml of ethyl acetate, was added to N,O-bis-trimethylsilyl 7-aminocephalosporanate (prepared from 1082 mg of 7-ACA).

After the reaction and working up the reactionmixture, 980 mg of a cristalline product, 7-{[3-methyl-4-chloroisoxazole-5 yl] acetamido} cephalosporanic acid, the alleged structure of which was confirmed by IR- and PMR-spectra, were isolated.

The corresponding sodium salt was prepared by dissolving the pure acid at room temperature in about 20 ml of acetone in the dark.

Under stirring a calculated amount of sodium-hexanoate solution was added dropwise.

The jelly-like pulp was cooled at about −15° C during two hours and filtrated.

The precipitate, which could easily be filtrated, was washed three times with acetone and at last once with diethyl ether.

After drying 930 mg of white solid; sodium 7-{[3-methyl-4-chloroisoxazole-5 yl] acetamido}-3 acetoxy methyl-3-cephem-4 carboxylate were obtained, having an Rf value of 0.5 with TLC (acetone/acetic acid 95/5; iodoazide/starch).

EXAMPLE XXXVI

The sodium salt of 7-{[3-methyl-isoxazol-5-yl]-acetamido}cephalosporanic acid (Example XXII) was tested for anti-bacterial activity in the following in vivo experiments.

a. in a protection test, the $ED_{50}$-values of the said sodium salt and of cephalotin (as reference compound) were estimated as listed below:

test animal: female mice (Swiss SPF) 10 mice pro grop of the same dose
infection: intraperitoneal administration of Staphylococcus aureus A 2001
Dose of test compound: 5 times per day
Duration of treatment: one day
Duration of observation: 7 days
Parameter:
$ED_{50}$-values (probit analysis)
Potency ratio (probit analysis)

Results

| Test Compound | Method of Administration | $ED_{50}$ in mg/kg | Potency Ratio |
|---|---|---|---|
| Ex. XXII | subcutaneously | 23 (10–52) | 1.90 |
| Cephalotin | subcutaneously | 43 (12–155) | (0.73–4.92) | b. In a similar experiment with regard to the protection by the same compounds after intraperitoneal administration of Escherichia coli 65161, the following results were obtained:

| Test Compound | Method of Administration | ED$_{50}$ in mg/kg | Potency Ratio |
|---|---|---|---|
| Ex. XXII | intraperitoneal | 100(56–178) | 1.15 |
| Cephalotin | intraperitoneal | 115(63–207) | (0.52–2.53) | c. The blood and urine contents of the above sodium salt and the same reference compound were determined after the intramuscular administration of an aqueous solution in rabbits (Nieuw Zeelander ♀ ♀, weight 1.95–2.2 kg). The rabbits were provided with "Cunicon" and water ad libitum. Each test group consisted of 3 rabbits. The dose was 50 mg/kg using water as the vehicle. Blood samples were taken after ¼, ½, 1, 2, 4 hours and Urine samples were taken after 1, 3, 6, 24, 27 hours (in practice only the total secreted amounts after 6 and 27 hours were used).

The contents of the compound in the samples were determined microbiologically (only microbiologically detected amounts, i.e. anti-bacterially active concentrations only have been indicated).

The test organisms were Bacillus subtilis AA and Bacillus subtilis 6633 and the results are listed in the table below:

| Results (average) | | XXII | Cephalotin | Distinction of statistically significant + non significant − | t-value |
|---|---|---|---|---|---|
| Serum level in mcg/ml after | ¼ hr. | 57.5 mcg/ml | 73.8 mcg/ml | − | 0.60 |
| | ½ hr. | 45.0 mcg/ml | 33.9 mcg/ml | − | 0.50 |
| | 1 hr. | 12.3 mcg/ml | 8.5 mcg/ml | − | 0.79 |
| | 2 hrs. | 1.7 mcg/ml | < 1.1 mcg/ml | − | 1.31 |
| | 4 hrs. | << 1 | << 1 | − | − |
| Secretion of compound in urine in % of the administered dose after | 6 hrs. | 41.4% | 22.2% | − | 1.79 |
| | 27 hrs. | 46.9% | 26.9% | + | 2.89 | d. For both compounds the percentages of bound serum were determined by ultrafiltration and dialysis:

| | XXII | Cephalotin |
|---|---|---|
| ultrafiltration | 33% | ± 70% |
| dialysis | 28% | ± 70% | e. The acute toxicity (LD$_{50}$ value) was determined to be >8.000 mg/kg for the above identified sodium salt while for cephalotin, LD$_{50}$ values of 6000–8000 mg/kg in mice after intraperitoneal administration were found.

Various modifications of the products and processes of the invention may be made without departing from the spirit or scope thereof and it is to be understood that the invention is to be limited only as defined in the appended claims.

We claim:

1. A compound of the formula

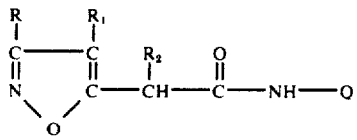

wherein R is lower alkyl of 1 to 4 carbon atoms, R$_1$ is selected from the group consisting of hydrogen, lower alkyl of 1 to 4 carbon atoms, cyano, amino and chlorine, R$_2$ is selected from the group consisting of hydrogen, amino, lower alkyl of 1 to 4 carbon atoms, bromo and chloro and Q is

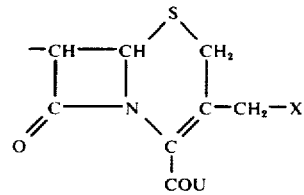

wherein X is selected from the group consisting of hydrogen, hydroxy and lower alkanoyloxy and U is OY, wherein Y is selected from the group consisting of hydrogen and non-toxic, pharmaceutically acceptable salt forming groups and alkyl of 1 to 4 carbon atoms.

2. A compound of claim 1, wherein R is selected from the group consisting of methyl, R$_1$ and R$_2$ are selected from the group consisting of hydrogen and methyl and K is acetoxy, and non-toxic, pharmaceutically acceptable salts and alkyl esters of 1 to 4 carbon atoms non-toxic, pharmaceutically acceptable.

3. A compound of claim 1 selected from the group consisting of 7-{[3-methyl-isoxazole-5-yl] acetamido}-3-acetoxymethyl-3-cephem-4-carboxylic acid and its non-toxic, pharmaceutically acceptable salts.

4. A compound of claim 1 selected from the group consisting of 7-{[3-methyl-4-chloro-isoxazole-5-yl] acetamido}3-acetoxy methyl-3-cephem-4-carboxylic acid and its non-toxic, pharmaceutically acceptable salts.

5. A compound of claim 1 selected from the group consisting of 7-{[3-t-butyl-isoxazole-5-yl] acetanido}3-acetoxymethyl-3-cephem-4-carboxylic acid and its non-toxic, pharmaceutically acceptable salts.

6. An antibacterial composition comprised of an bactericidally effective amount of a compound of the formula

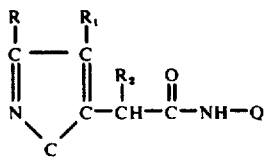

wherein R is lower alkyl of 1 to 4 carbon atoms, $R_1$ is selected from the group consisting of hydrogen, lower alkyl of 1 to 4 carbon atoms, cyano, amino and chlorine, $R_2$ is selected from the group consisting of hydrogen, amino, lower alkyl of 1 to 4 carbon atoms, bromo and chloro, and Q is

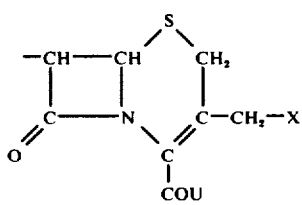

wherein X is selected from the group consisting of hydrogen, hydroxy and lower alkanoyloxy and U is OY, wherein Y is selected from the group consisting of hydrogen and non-toxic, pharmaceutically acceptable salt forming groups and alkyl of 1 to 4 carbon atoms and a pharmaceutical carrier.

7. A method of combatting bacteria which comprises contacting bacteria with a bactericidally effective amount of a compound of the formula

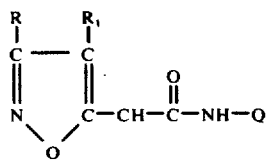

wherein R is lower alkyl of 1 to 4 carbon atoms, $R_1$ is selected from the group consisting of hydrogen, lower alkyl of 1 to 4 carbon atoms, cyano, amino and chlorine, $R_2$ is selected from the group consisting of hydrogen, amino, lower alkyl of 1 to 4 carbon atoms, bromo and chloro and Q is

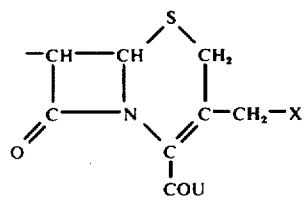

wherein X is selected from the group consisting of hydrogen, hydroxy and lower alkanoyloxy and U is OY, wherein Y is selected from the group consisting of hydrogen and non-toxic, pharmaceutically acceptable salt forming groups and alkyl of 1 to 4 carbon atoms.

8. A method of combatting bacterial infections in warm-blooded animals, inclusive human beings, which comprises administering to said warm-blooded animals a bactericidally effective amount of a compound of the formula

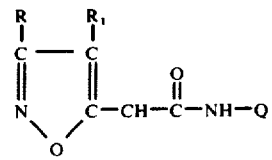

wherein R is lower alkyl of 1 to 4 carbon atoms, $R_1$ is selected from the group consisting of hydrogen, lower alkyl of 1 to 4 carbon atoms, cyano, amino and chlorine, $R_2$ is selected from the group consisting of hydrogen, amino, lower alkyl of 1 to 4 carbon atoms, bromo and chloro and Q is

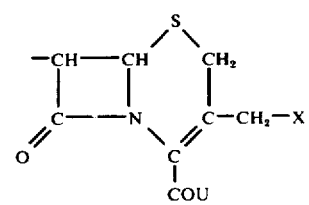

wherein X is selected from the group consisting of hydrogen, hydroxy and lower alkanoyloxy and U is OY, wherein Y is selected from the group consisting of hydrogen and non-toxic, pharmaceutically acceptable salt forming groups and alkyl of 1 to 4 carbon atoms.

9. An antibacterial composition comprised of a bactericidally effective amount of a compound of the formula

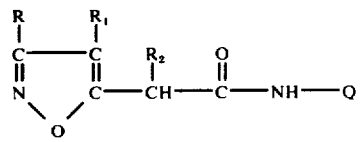

wherein R is selected from the group consisting of mono aminophenyl, mono nitrophenyl, phenyl and phenyl substituted with one to three members of the group consisting of chlorine, fluorine and lower alkyl of 1 to 4 carbon atoms, $R_1$ is selected from the group consisting of hydrogen, lower alkyl of 1 to 4 carbon atoms, carbamyl, cyano, amino and chlorine $R_2$ is selected from the group consisting of hydrogen, amino, lower alkyl of 1 to 4 carbon atoms, bromo and chloro and Q is

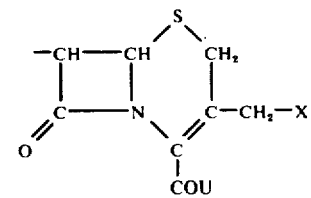

wherein X is selected from the group consisting of hydrogen, hydroxy and lower alkanoyloxy and U is OY, wherein Y is selected from the group consisting of hydrogen and non-toxic, pharmaceutically acceptable salt forming groups and alkyl of 1 to 4 carbon atoms and a pharmaceutical carrier.

10. A method of combatting bacteria which comprises contacting bacteria with a bactericidally effective amount of a compound of the formula

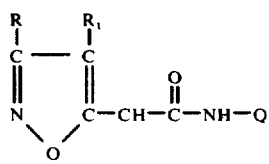

wherein R is selected from the group consisting of mono aminophenyl, mono nitrophenyl, phenyl and phenyl substituted with one to three members of the group consisting of chlorine, fluorine and lower alkyl of 1 to 4 carbon atoms, $R_1$ is selected from the group consisting of hydrogen, lower alkyl of 1 to 4 carbon atoms, carbamyl, cyano, amino and chlorine, $R_2$ is selected from the group consisting of hydrogen, amino, lower alkyl of 1 to 4 carbon atoms, bromo and chloro and Q is

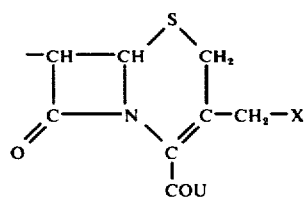

wherein X is selected from the group consisting of hydrogen, hydroxy and lower alkanoyloxy and U is OY, wherein Y is selected from the group consisting of hydrogen and non-toxic, pharmaceutically acceptable salt forming groups and alkyl of 1 to 4 carbon atoms.

11. A method of combatting bacterial infections in warm-blooded animals which comprises administering to warm-blooded animals a bactericidally effective amount of a compound of the formula

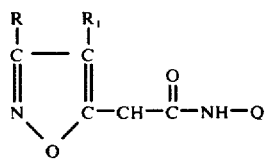

wherein R is selected from the group consisting of mono aminophenyl, mono nitrophenyl, phenyl and phenyl substituted with one to three members of the group consisting of chlorine, fluorine and lower alkyl 1 to 4 carbon atoms, $R_1$ is selected from the group consisting of hydrogen, lower alkyl of 1 to 4 carbon atoms, carbamyl, cyano, amino and chlorine, $R_2$ is selected from the group consisting of hydrogen, amino, lower alkyl of 1 to 4 carbon atoms, bromo and chloro and Q is

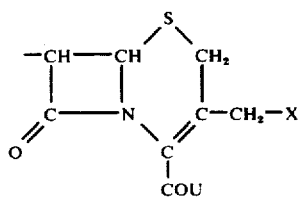

wherein X is selected from the group consisting of hydrogen, hydroxy and lower alkanoyloxy and U is OY, wherein Y is selected from the group consisting of hydrogen and non-toxic, pharmaceutically acceptable salt forming groups and alkyl of 1 to 4 carbon atoms.

* * * * *